(12) United States Patent
Summers et al.

(10) Patent No.: US 10,883,088 B2
(45) Date of Patent: Jan. 5, 2021

(54) BIOLOGICAL UPGRADING OF HYDROCARBON STREAMS WITH OXYGENASES

(71) Applicant: ExxonMobil Research and Engineering Company, Annandale, NJ (US)

(72) Inventors: Zarath M. Summers, High Bridge, NJ (US); David O. Marler, Easton, PA (US); Jay B. Patel, Princeton, NJ (US); Katherine G. Landuyt, Dallas, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/186,789

(22) Filed: Nov. 12, 2018

(65) Prior Publication Data
US 2019/0177703 A1     Jun. 13, 2019

Related U.S. Application Data

(60) Provisional application No. 62/597,502, filed on Dec. 12, 2017.

(51) Int. Cl.
| C12N 9/02 | (2006.01) |
| C12N 11/08 | (2020.01) |
| C07K 14/795 | (2006.01) |
| C10G 32/00 | (2006.01) |

(52) U.S. Cl.
CPC .......... *C12N 9/0069* (2013.01); *C07K 14/795* (2013.01); *C10G 32/00* (2013.01); *C12N 11/08* (2013.01); *C10G 2300/1077* (2013.01); *C10G 2300/202* (2013.01); *C10G 2300/80* (2013.01)

(58) Field of Classification Search
None
See application file for complete search history.

(56) References Cited

U.S. PATENT DOCUMENTS

| 5,297,625 A | 3/1994 | Premuzic et al. |
| 5,492,828 A | 2/1996 | Premuzic et al. |
| 5,624,844 A * | 4/1997 | Xu .......................... C10G 1/00 435/264 |
| 5,726,056 A | 3/1998 | Xu et al. |
| 5,858,766 A | 1/1999 | Premuzic et al. |
| 5,885,825 A | 3/1999 | Lin et al. |
| 7,041,814 B1 | 9/2006 | Weinstock et al. |
| 8,475,652 B2 | 7/2013 | Paul et al. |
| 2011/0039164 A1 | 2/2011 | Akers et al. |
| 2011/0089083 A1 | 4/2011 | Paul et al. |
| 2016/0160105 A1 | 6/2016 | Dhulipala et al. |
| 2016/0333307 A1 | 11/2016 | Fong et al. |

FOREIGN PATENT DOCUMENTS

| JP | 9176168 A | 7/1999 |
| JP | 11187890 A | 7/1999 |
| JP | 2000069958 A | 3/2000 |
| WO | 20160053648 A1 | 4/2016 |

OTHER PUBLICATIONS

D'Antonio et al., "Degradation of Petroporphyrin Mimics by Heme Oxygenase" [Abstract], 60th American Chemical Society Southeast Regional Meeting, 2008.
Dedeles et al., "Microbial Demetallizaiton of Crude Oil: Nickel Protoporphyrin Disodium as a Model Organo-Metallic Substrate", Journal of Bioscience and Bioengineering, 2000, 90, 515-521.
Mogollon et al., "Fraccionamiento Y Desmetalizacion Biocatalitica De Asfaltenos De Crudo Castilla", Ciencia Tecnologia y Futuro, 1997, 1, 109-121 (English Abstract Only).
Smith et al., "Vanadium and Nickel Porphyrin Removal From Refinery Residual Under Mild Conditions", Preprints American Chemical Society Division of Petroleum Chemistry, 2012, 57, 159.
The International Search Report and Written Opinion of PCT/US2018/060261 dated Apr. 17, 2019.

* cited by examiner

*Primary Examiner* — Anand U Desai
(74) *Attorney, Agent, or Firm* — Amanda K. Norwood; Kristina Okafor

(57) ABSTRACT

Oxygenases and methods of biologically upgrading hydrocarbon streams, such as crude oil, using oxygenases are provided herein. The oxygenases can be used to remove impurities such as metals, heteroatoms, or asphaltenes from a hydrocarbon stream. In some cases, the oxygenases can be chemically or genetically modified and can be used in different locations such as petroleum wells, pipes, reservoirs, tanks and/or reactors.

24 Claims, 6 Drawing Sheets

Specification includes a Sequence Listing.

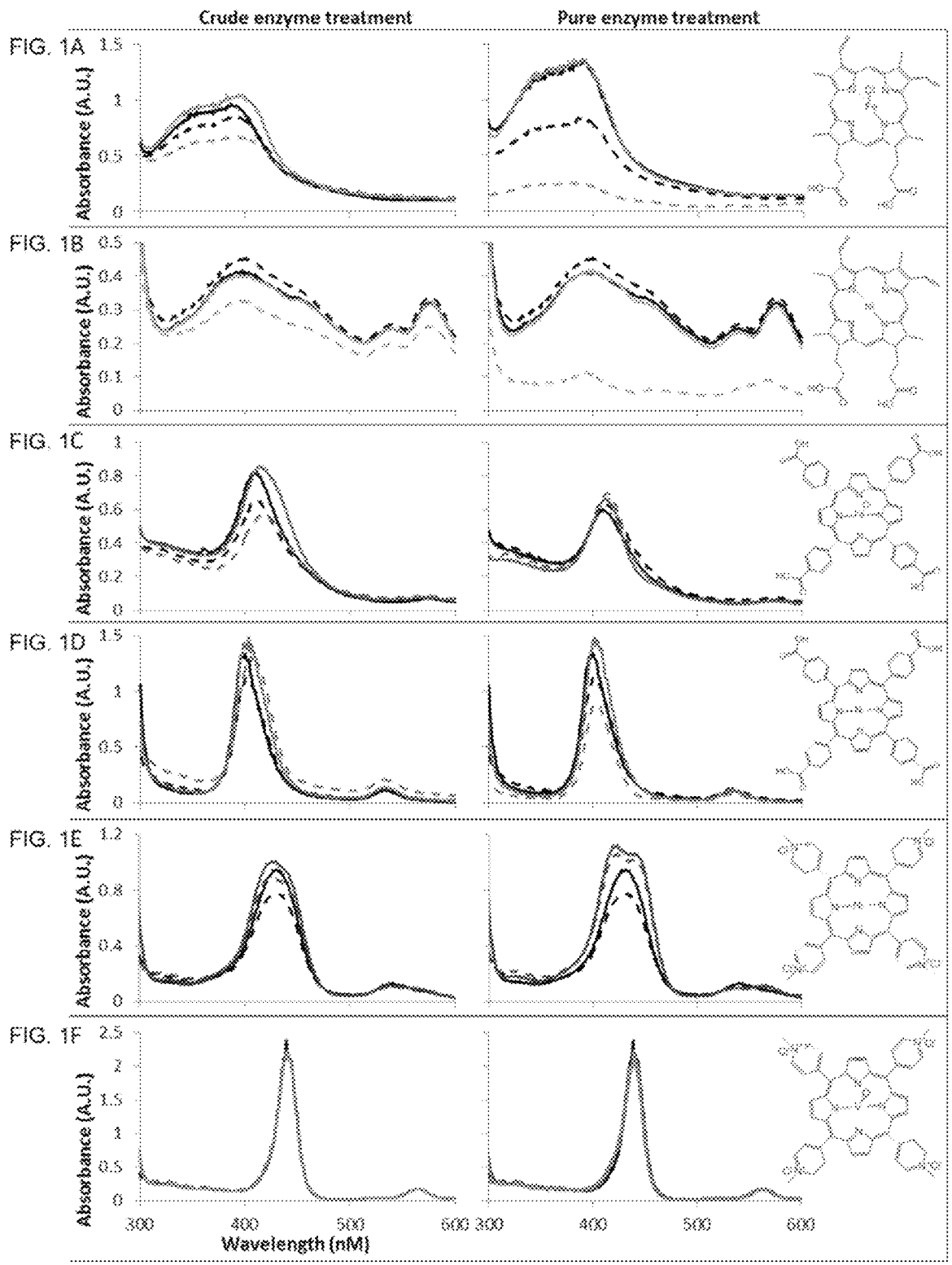

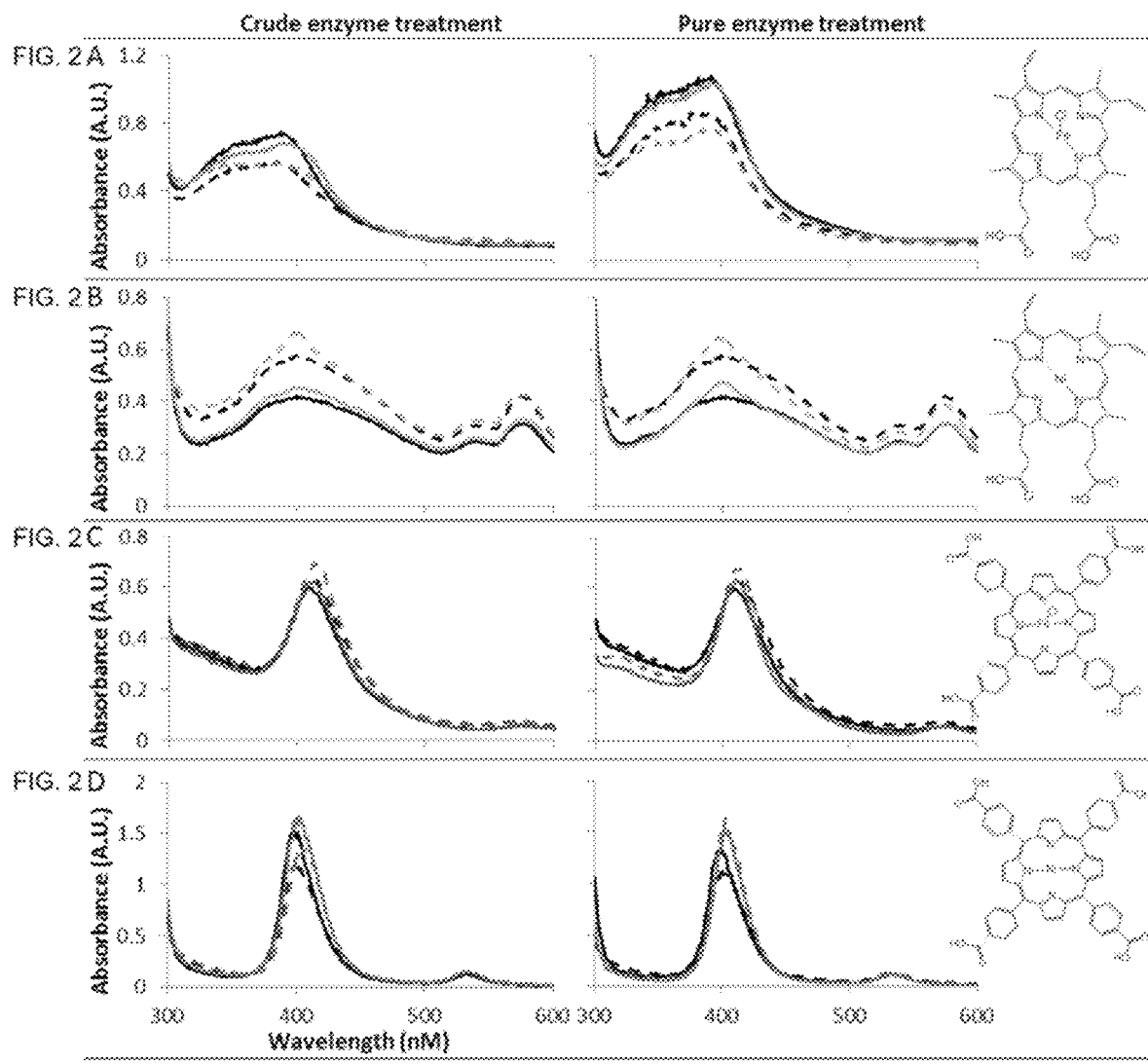

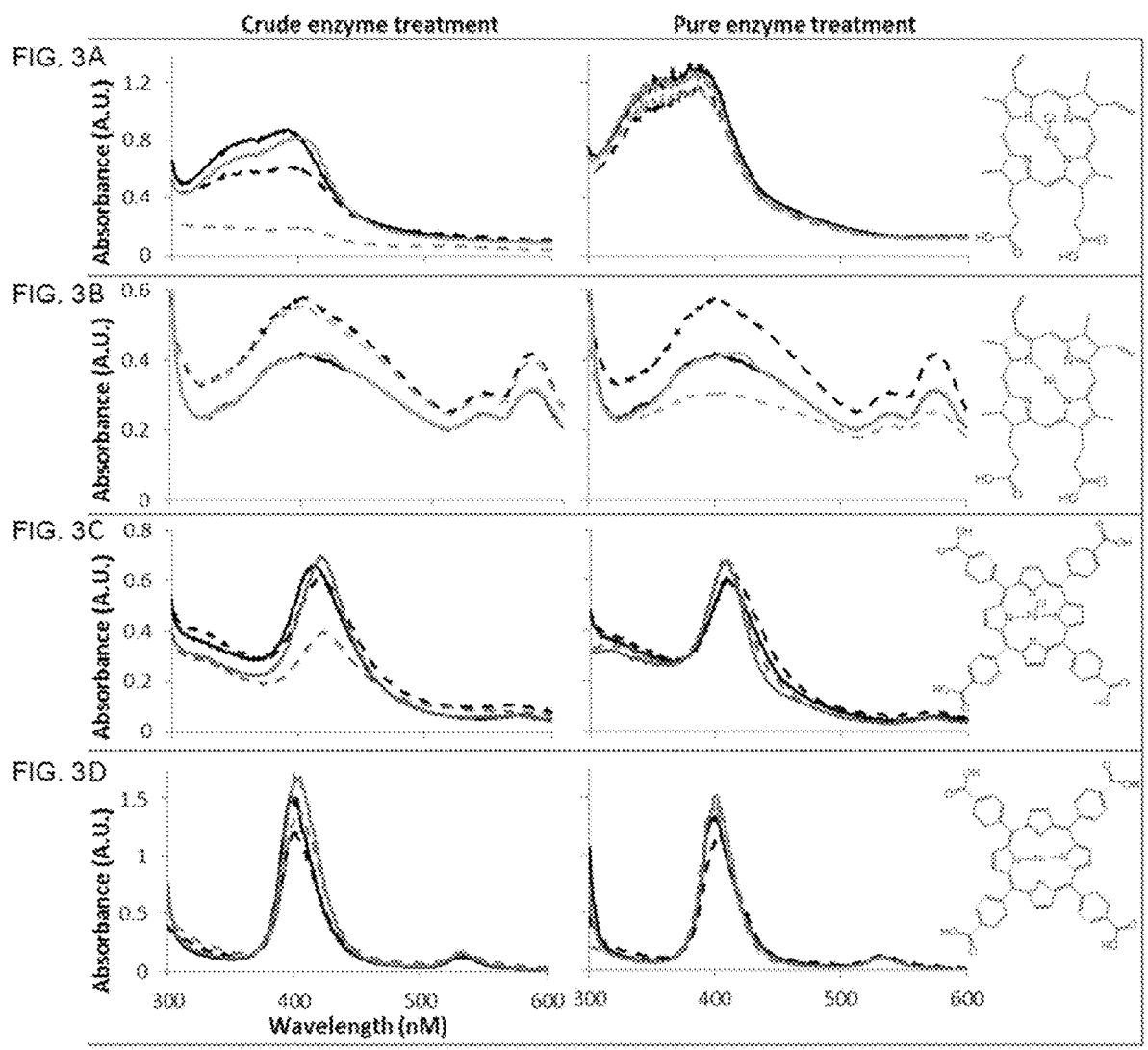

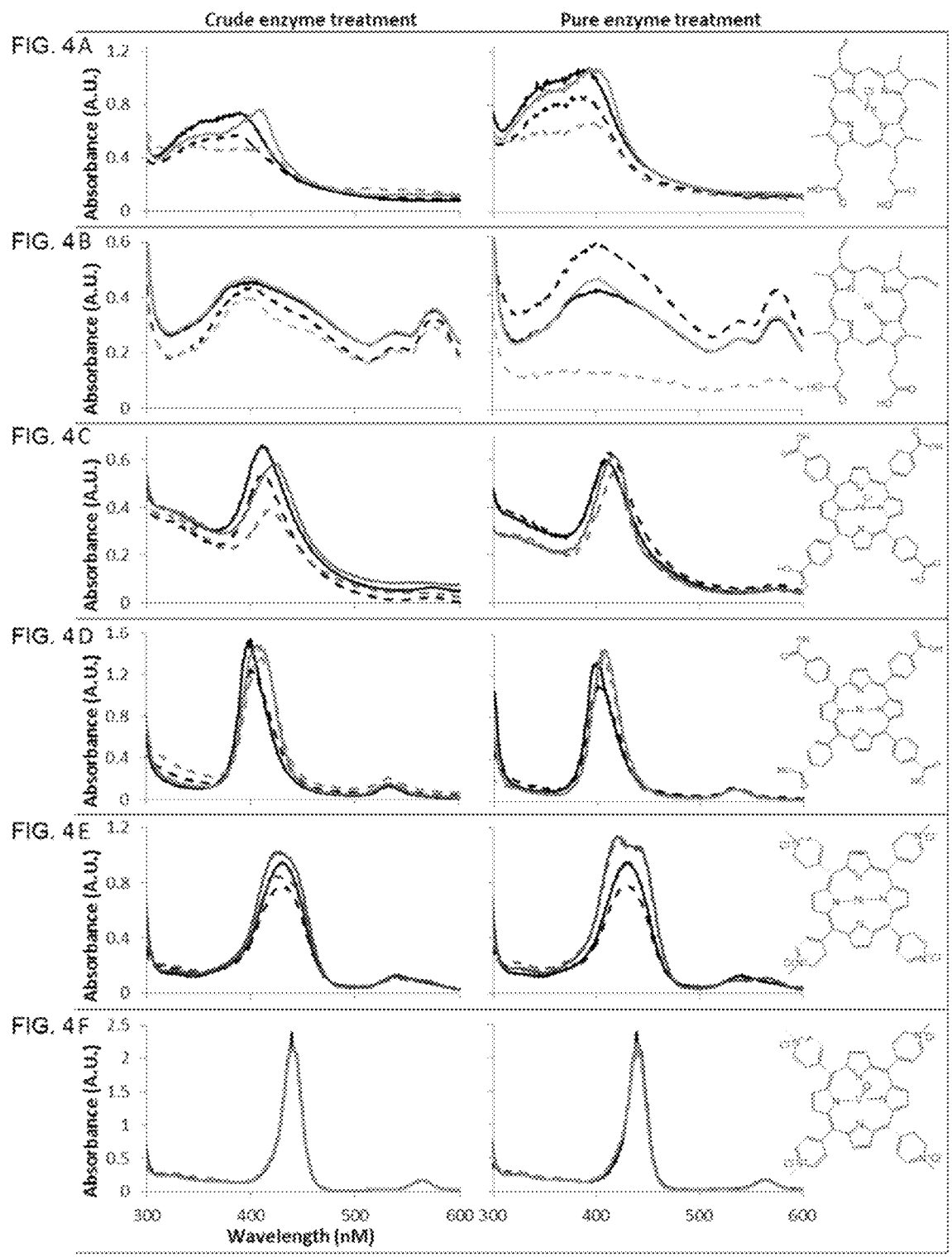

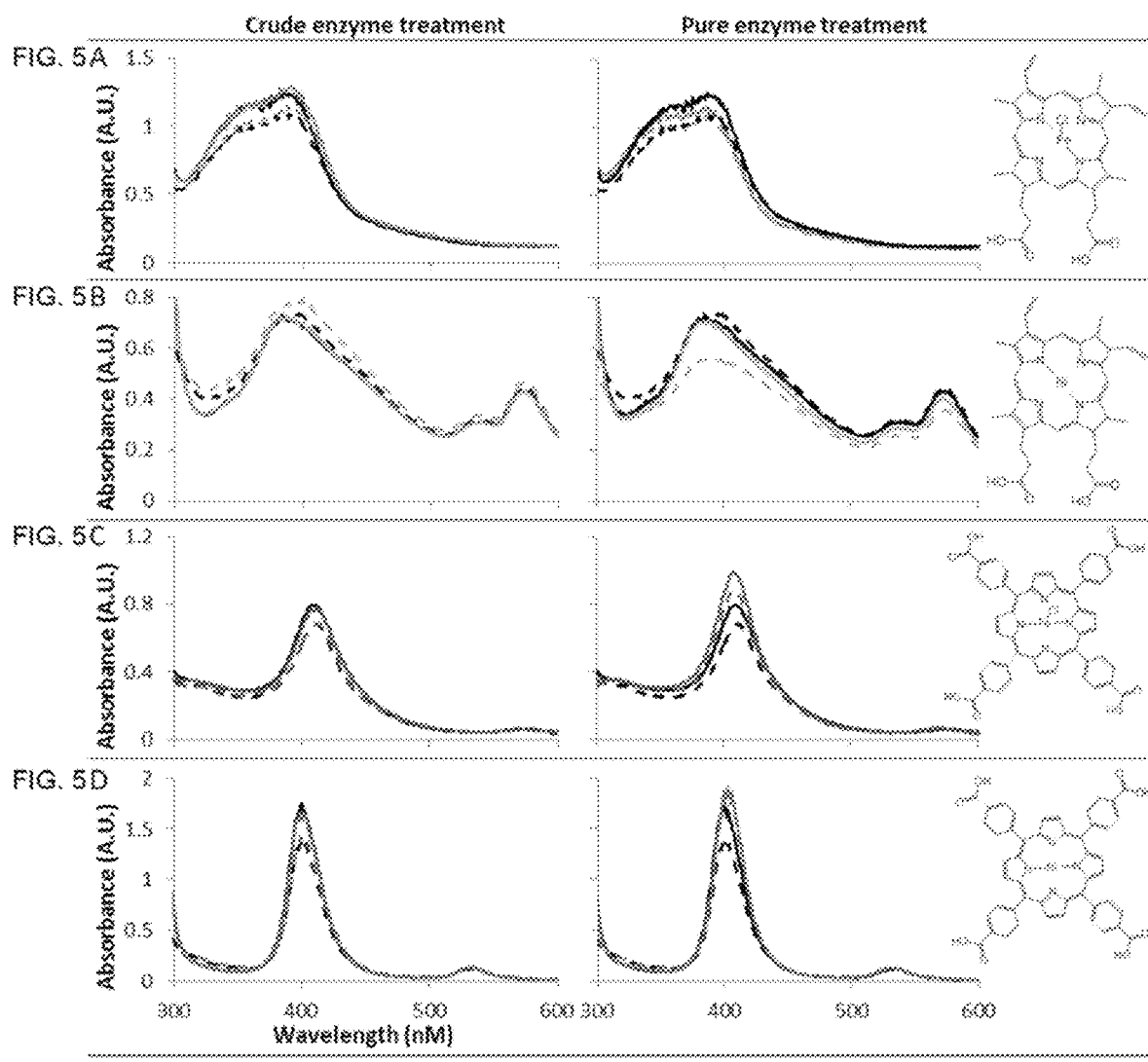

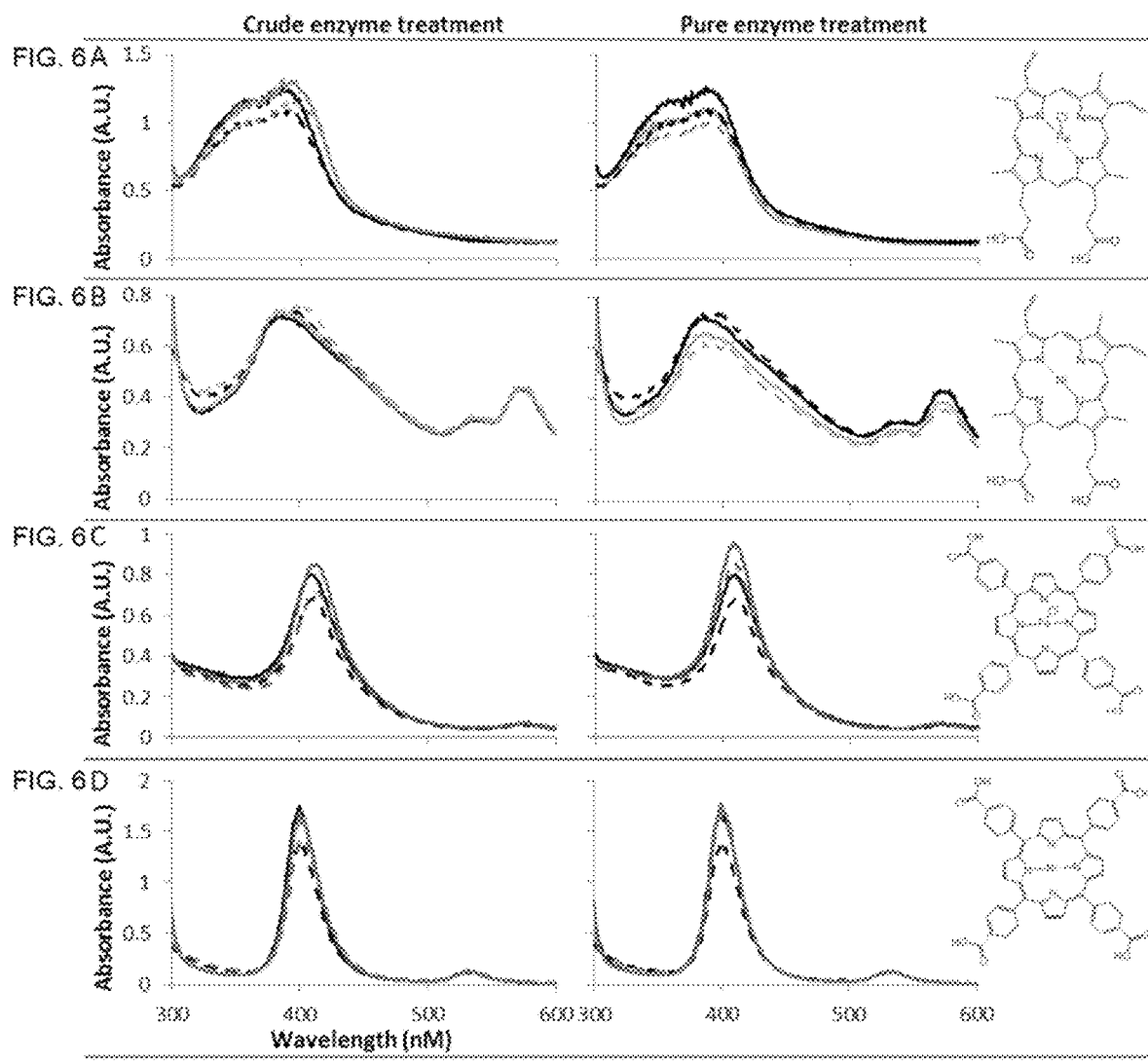

SEQUENCE LISTING

<160> NUMBER OF SEQ ID NOS: 14

<210> SEQ ID NO 1
<211> LENGTH: 224
<212> TYPE: PRT
<213> ORGANISM: Corynebacterium jeikeium

<400> SEQUENCE: 1

```
Met Ala Ser Thr Ser Thr Leu Ser Asn Thr Ser Phe Asn Thr Ala Glu
1               5                   10                  15

Pro Ile Ser Gln Ala Leu Arg Asn Ala Thr Ala Glu Ala His Gly Arg
            20                  25                  30

Ala Glu Gly Ser Glu Phe Met Ser Thr Leu Phe Lys Gly Glu Leu Asp
        35                  40                  45

Ala Gln Ala Val Tyr Ala Leu Ser Gly Gln Leu Trp Phe Val Tyr Ser
    50                  55                  60

Ala Leu Glu Asn Ala Val Glu Arg Val Ser Gly Thr Pro Ile Gly Ser
65                  70                  75                  80

Val Ile Ala Asp Pro Arg Leu Gln Arg Cys Ala Ala Leu Glu His Asp
                85                  90                  95

Leu Thr Tyr Cys Leu Gly Ser Asp Trp Arg Glu Gln Leu Glu Leu Leu
            100                 105                 110

Pro Ala Thr Arg Arg Tyr Val Asp Arg Leu Asp Ser Phe Gly Glu Gln
        115                 120                 125

Asp Val Val Arg Val Ile Ala His His Tyr Val Arg Tyr Leu Gly Asp
    130                 135                 140

Ile Ser Gly Gly Gln Val Ile Ala Val Arg Val Ala Asp Leu Tyr Asn
145                 150                 155                 160

Val Ala Pro Glu Ala Leu Lys Phe Tyr Asp Phe Ser Ala Ile Gly Lys
                165                 170                 175

Ile Pro Pro Tyr Arg Thr Ser Tyr Arg Gln Arg Leu Asp Ser Leu Pro
            180                 185                 190

Leu Thr Ala Gln Gln Arg Ser Glu Leu Ile Glu Glu Ala Ile Asp Ala
        195                 200                 205

Phe Gly Met Asn Phe Ser Leu Phe Thr Asp Leu Tyr Gly Val Cys Ala
    210                 215                 220
```

<210> SEQ ID NO 2
<211> LENGTH: 198
<212> TYPE: PRT
<213> ORGANISM: Pseudomonas aeruginosa

<400> SEQUENCE: 2

```
Met Asp Thr Leu Ala Pro Glu Ser Thr Arg Gln Asn Leu Arg Ser Gln
1               5                   10                  15

Arg Leu Asn Leu Leu Thr Asn Glu Pro His Gln Arg Leu Glu Ser Leu
            20                  25                  30

Val Lys Ser Lys Glu Pro Phe Ala Ser Arg Asp Asn Phe Ala Arg Phe
        35                  40                  45

Val Ala Ala Gln Tyr Leu Phe Gln His Asp Leu Glu Pro Leu Tyr Arg
    50                  55                  60

Asn Glu Ala Leu Ala Arg Leu Phe Pro Gly Leu Ala Ser Arg Ala Arg
65                  70                  75                  80

Asp Asp Ala Ala Arg Ala Asp Leu Ala Asp Leu Gly His Pro Val Pro
                85                  90                  95

Glu Gly Asp Gln Ser Val Arg Glu Ala Asp Leu Ser Leu Ala Glu Ala
            100                 105                 110

Leu Gly Trp Leu Phe Val Ser Glu Gly Ser Lys Leu Gly Ala Ala Phe
        115                 120                 125

Leu Phe Lys Lys Ala Ala Ala Leu Glu Leu Asp Glu Asn Phe Gly Ala
    130                 135                 140
```

```
Arg His Leu Ala Glu Pro Glu Gly Arg Ala Gln Gly Trp Lys Ser
145                 150                 155                 160

Phe Val Ala Ile Leu Asp Gly Ile Glu Leu Asn Glu Glu Glu Arg
                165                 170                 175

Leu Ala Ala Lys Gly Ala Ser Asp Ala Phe Asn Arg Phe Gly Asp Leu
            180                 185                 190

Leu Glu Arg Thr Phe Ala
        195

<210> SEQ ID NO 3
<211> LENGTH: 342
<212> TYPE: PRT
<213> ORGANISM: Escherichia coli

<400> SEQUENCE: 3

Met Asn His Tyr Thr Arg Trp Leu Glu Leu Lys Glu Gln Asn Pro Gly
1               5                   10                  15

Lys Tyr Ala Arg Asp Ile Ala Gly Leu Met Asn Ile Ser Glu Ala Glu
            20                  25                  30

Leu Ala Phe Ala Arg Val Thr His Asp Ala Trp Arg Met Arg Gly Asp
        35                  40                  45

Ile Arg Glu Ile Leu Ala Ala Leu Glu Ser Val Gly Glu Thr Lys Cys
50                  55                  60

Ile Cys Arg Asn Glu Tyr Ala Val His Glu Val Gly Val Ala Phe Thr
65                  70                  75                  80

Asn Gln His Leu Asn Gly His Ala Gly Leu Ile Leu Asn Pro Arg Ala
                85                  90                  95

Leu Asp Leu Arg Leu Phe Leu Asn Gln Trp Ala Ser Val Phe His Ile
            100                 105                 110

Lys Glu Asn Thr Ala Arg Gly Glu Arg Gln Ser Ile Gln Phe Phe Asp
        115                 120                 125

His Gln Gly Asp Ala Leu Leu Lys Val Tyr Ala Thr Asp Asn Thr Asp
    130                 135                 140

Met Ala Ala Trp Ser Glu Leu Leu Ala Arg Phe Ile Thr Asp Glu Asn
145                 150                 155                 160

Thr Pro Leu Glu Leu Lys Ala Val Asp Ala Pro Val Val Gln Thr Arg
                165                 170                 175

Ala Asp Ala Ser Val Val Glu Gln Glu Trp Arg Ala Met Thr Asp Val
            180                 185                 190

His Gln Phe Phe Thr Leu Leu Lys Arg His Asn Leu Thr Arg Gln Gln
        195                 200                 205

Ala Phe Asn Leu Val Ala Asp Asp Leu Ala Cys Lys Val Ser Asn Ser
    210                 215                 220

Ala Leu Ala Gln Ile Leu Glu Ser Ala Gln Gln Asp Gly Asn Glu Ile
225                 230                 235                 240

Met Val Phe Val Gly Asn Arg Gly Cys Val Gln Ile Phe Thr Gly Val
                245                 250                 255

Val Glu Lys Val Val Pro Met Lys Gly Trp Leu Asn Ile Phe Asn Pro
            260                 265                 270

Thr Phe Thr Leu His Leu Leu Glu Ser Ile Ala Glu Thr Trp Val
        275                 280                 285

Thr Arg Lys Pro Ala Ser Asp Gly Tyr Val Thr Ser Leu Glu Leu Phe
    290                 295                 300

Ala His Asp Gly Thr Gln Ile Ala Gln Leu Tyr Gly Gln Arg Thr Glu
```

```
                    305                 310                 315                 320
Gly Glu Gln Glu Gln Ala Gln Trp Arg Lys Gln Ile Ala Ser Leu Ile
                    325                 330                 335

Pro Glu Gly Val Thr Ala
                340

<210> SEQ ID NO 4
<211> LENGTH: 360
<212> TYPE: PRT
<213> ORGANISM: Pseudomonas aeruginosa

<400> SEQUENCE: 4

His His His His His His Met Ser Ser Thr Pro Ser Leu Ser His Ser
 1               5                  10                  15

Pro Ala Glu Leu Tyr Arg Ala Trp Gln Asp Leu Arg Ala Glu Arg Pro
                20                  25                  30

Gln Leu Arg Ala Arg Asp Ala Ala Leu Leu Gln Val Ser Glu Gly
                35                  40                  45

Glu Leu Val Ala Ser Arg Val Gly Ile Asp Ala Val Arg Leu Arg Pro
        50                  55                  60

Asp Trp Ala Ala Leu Leu Pro Ala Leu Gly Glu Leu Gly Pro Ile Met
65                  70                  75                  80

Ala Leu Thr Arg Asn Glu His Cys Val His Glu Arg Lys Gly Pro Tyr
                85                  90                  95

Arg Glu Val Thr Val Ser Ala Asn Gly Gln Met Gly Leu Val Val Ser
                100                 105                 110

Pro Asp Ile Asp Leu Arg Leu Phe Leu Gly Gly Trp Asn Ala Val Phe
                115                 120                 125

Ala Ile Ala Glu Glu Thr Ala Arg Gly Thr Gln Arg Ser Ile Gln Val
        130                 135                 140

Phe Asp Gln Gln Gly Val Ala Val His Lys Val Phe Leu Ala Glu Ala
145                 150                 155                 160

Ser Asp Val Arg Ala Trp Glu Pro Leu Val Glu Arg Leu Arg Ala Ala
                165                 170                 175

Glu Gln Asp Ala Val Leu Ala Leu His Glu Pro Arg Ala Pro Ala Ala
                180                 185                 190

Ala Leu Val Asp Ala Gln Ile Asp Ala Ala Leu Arg Glu Gly Trp
        195                 200                 205

Ala Ala Leu Lys Asp Thr His His Phe His Ala Leu Leu Lys Lys His
210                 215                 220

Gly Ala Gln Arg Thr Gln Ala Leu Arg Leu Ala Gly Gly Glu Trp Ala
225                 230                 235                 240

Glu Arg Leu Asp Asn Gly Asp Leu Ala Lys Leu Phe Glu Ala Ala Ala
                245                 250                 255

Glu Ser Gly Leu Pro Ile Met Val Phe Val Gly Asn Ala His Cys Ile
                260                 265                 270

Gln Ile His Thr Gly Pro Val Cys Asn Leu Lys Trp Leu Asp Asp Trp
        275                 280                 285

Phe Asn Val Leu Asp Pro Glu Phe Asn Leu His Leu Lys Thr Thr Gly
        290                 295                 300

Ile Ala Glu Leu Trp Arg Val Arg Lys Pro Ser Thr Asp Gly Ile Val
305                 310                 315                 320

Thr Ser Trp Glu Ala Phe Asp Pro Asp Gly Glu Leu Ile Val Gln Leu
                325                 330                 335
```

```
Phe Gly Ala Arg Lys Pro Gly Glu Pro Glu Arg Asp Asp Trp Arg Glu
            340                 345                 350

Leu Ala Glu Ser Phe Lys Ala Leu
        355                 360

<210> SEQ ID NO 5
<211> LENGTH: 251
<212> TYPE: PRT
<213> ORGANISM: Helicobacter pylori

<400> SEQUENCE: 5

Met Leu Asn Arg Ile Ile Glu His Met Asn Ala His Val Glu Asp
1               5                   10                  15

Met Lys Gly Leu Leu Lys Lys Phe Gly Gln Val His Ala Glu Asn
                20                  25                  30

Val Ala Phe Lys Ser Val Asp Ser Gln Gly Val Val Ile Gly Tyr Asn
                35                  40                  45

Asn Asn Gln Thr Leu Arg Ile Glu Phe Asn His Glu Val Lys Asp Pro
            50                  55                  60

Lys Asp Tyr Lys Asn Ala Ile Ile Glu Leu Cys Gln Ser Val Glu Lys
65                  70                  75                  80

Thr His Asp Leu Lys Gly Val Glu Glu Val Lys Ala Phe Lys Glu
                    85                  90                  95

Gly Phe Asp Ser Val Cys Leu Ala Thr Leu His Pro Asn Gly His Val
                100                 105                 110

Val Cys Ser Tyr Ala Pro Leu Met Ser Asp Gly Lys Gln Tyr Tyr Ile
                115                 120                 125

Tyr Val Ser Glu Val Ala Glu His Phe Ala Gly Leu Lys His Asn Pro
            130                 135                 140

His Asn Val Glu Val Met Phe Leu Glu Asp Glu Ser Lys Ala Lys Ser
145                 150                 155                 160

Ala Ile Leu Arg Lys Arg Leu Arg Tyr Lys Thr Asn Ala Arg Phe Ile
                165                 170                 175

Glu Arg Gly Ala Glu Phe Asp Lys Ala Phe Asp Ser Phe Ile Glu Lys
                180                 185                 190

Thr Gly Gly Ala Gly Gly Ile Lys Thr Ile Arg Thr Met Gln Asp Phe
            195                 200                 205

His Leu Ile Ala Leu Asp Phe Lys Glu Gly Arg Phe Val Lys Gly Phe
    210                 215                 220

Gly Gln Ala Tyr Asp Ile Leu Gly Asp Lys Ile Ala Tyr Val Gly Asp
225                 230                 235                 240

Lys Gly Asn Pro His Asp Phe Ala His Lys Lys
                245                 250

<210> SEQ ID NO 6
<211> LENGTH: 108
<212> TYPE: PRT
<213> ORGANISM: Staphylococcus aureus

<400> SEQUENCE: 6

Met Phe Met Ala Glu Asn Arg Leu Gln Leu Gln Lys Gly Ser Ala Glu
1               5                   10                  15

Glu Thr Ile Glu Arg Phe Tyr Asn Arg Gln Gly Ile Glu Thr Ile Glu
                20                  25                  30

Gly Phe Gln Gln Met Phe Val Thr Lys Thr Leu Asn Thr Glu Asp Thr
            35                  40                  45
```

Asp Glu Val Lys Ile Leu Thr Ile Trp Glu Ser Glu Asp Ser Phe Asn
    50                  55                  60

Asn Trp Leu Asn Ser Asp Val Phe Lys Glu Ala His Lys Asn Val Arg
65                  70                  75                  80

Leu Lys Ser Asp Asp Gly Gln Gln Ser Pro Ile Leu Ser Asn Lys
                85                  90                  95

Val Phe Lys Tyr Asp Ile Gly Tyr His Tyr Gln Lys
            100                 105

<210> SEQ ID NO 7
<211> LENGTH: 123
<212> TYPE: PRT
<213> ORGANISM: Mycobacterium tuberculosis

<400> SEQUENCE: 7

Met Pro Val Val Lys Ile Asn Ala Ile Glu Val Pro Ala Gly Ala Gly
1               5                   10                  15

Pro Glu Leu Glu Lys Arg Phe Ala His Arg Ala His Ala Val Glu Asn
            20                  25                  30

Ser Pro Gly Phe Leu Gly Phe Gln Leu Leu Arg Pro Val Lys Gly Glu
        35                  40                  45

Glu Arg Tyr Phe Val Val Thr His Trp Glu Ser Asp Glu Ala Phe Gln
    50                  55                  60

Ala Trp Ala Asn Gly Pro Ala Ile Ala Ala His Ala Gly His Arg Ala
65                  70                  75                  80

Asn Pro Val Ala Thr Gly Ala Ser Leu Leu Glu Phe Glu Val Val Leu
                85                  90                  95

Asp Val Gly Gly Thr Gly Lys Thr Ala Gly Val Pro Arg Gly Lys Leu
            100                 105                 110

Ala Ala Ala Leu Glu His His His His His His
        115                 120

<210> SEQ ID NO 8
<211> LENGTH: 165
<212> TYPE: PRT
<213> ORGANISM: Bacillus thuringiensis

<400> SEQUENCE: 8

Met Lys Ala Ile Ile Ser Tyr Glu Thr Pro Leu Glu Gln Ser His Phe
1               5                   10                  15

Thr Ala Lys Asn Asp Glu Lys Asn Met Phe Tyr Lys Glu Asn Thr Glu
            20                  25                  30

Glu Ser Val Glu Gly Ser Leu Gln Tyr Asp Val Leu Asp Ala Val Gly
        35                  40                  45

Glu Phe Lys Gly Gln Ser Gly Tyr Ile Val Cys Asn Asn Ile Ser Val
    50                  55                  60

Thr Asp Glu Gly Arg Pro Val Phe Glu Asn Arg Phe Lys Asn Arg Ala
65                  70                  75                  80

Gly Leu Ile Glu Asn Glu Pro Gly Phe Gln Ala Ile Arg Val Leu Arg
                85                  90                  95

Pro Leu Ser Asn Asp Thr Tyr Val Ile Leu Thr Met Trp Glu Thr Glu
            100                 105                 110

Gln Asn Phe Lys Asp Trp Thr Glu Ser Arg Ser Phe Glu Asn Ala His
        115                 120                 125

Lys Lys Arg Pro Thr Gln Ala Glu Gly Gln Ala Pro Ala His Pro His
    130                 135                 140

```
Ala Glu Gln Gln Lys Ser Ile Phe Ser Arg Pro Ser Phe Val Thr Thr
145                 150                 155                 160

Phe Asp Val Leu Val
                165
```

<210> SEQ ID NO 9
<211> LENGTH: 107
<212> TYPE: PRT
<213> ORGANISM: Staphylococcus aureus

<400> SEQUENCE: 9

```
Met Lys Phe Met Ala Glu Asn Arg Leu Thr Leu Thr Lys Gly Thr Ala
1               5                   10                  15

Lys Asp Ile Ile Glu Arg Phe Tyr Thr Arg His Gly Ile Glu Thr Leu
                20                  25                  30

Glu Gly Phe Asp Gly Met Phe Val Thr Gln Thr Leu Glu Gln Glu Asp
            35                  40                  45

Phe Asp Glu Val Lys Ile Leu Thr Val Trp Lys Ser Lys Gln Ala Phe
        50                  55                  60

Thr Asp Trp Leu Lys Ser Asp Val Phe Lys Ala Ala His Lys His Val
65                  70                  75                  80

Arg Ser Lys Asn Glu Asp Glu Ser Ser Pro Ile Ile Asn Asn Lys Val
                85                  90                  95

Ile Thr Tyr Asp Ile Gly Tyr Ser Tyr Met Lys
            100                 105
```

<210> SEQ ID NO 10
<211> LENGTH: 121
<212> TYPE: PRT
<213> ORGANISM: Listeria monocytogenes

<400> SEQUENCE: 10

```
Met Ile Ile Val Thr Asn Thr Ile Lys Val Glu Lys Gly Ala Ala Glu
1               5                   10                  15

His Val Ile Arg Gln Phe Thr Gly Ala Asn Gly Asp Gly His Pro Thr
                20                  25                  30

Lys Asp Ile Ala Glu Val Glu Gly Phe Leu Gly Phe Glu Leu Trp His
            35                  40                  45

Ser Lys Pro Glu Asp Lys Asp Tyr Glu Glu Val Val Val Thr Ser Lys
        50                  55                  60

Trp Glu Ser Glu Glu Ala Gln Arg Asn Trp Val Lys Ser Asp Ser Phe
65                  70                  75                  80

Lys Lys Ala His Gly Arg Thr Lys Asp Thr Arg Glu Gln Arg Glu Asp
                85                  90                  95

Arg Lys Gly Ile Val Gly Asn Ala Ile Ala Arg Phe Gly Val Val His
            100                 105                 110

Val Gln Asn Pro Val Ile Val Glu Lys
        115                 120
```

<210> SEQ ID NO 11
<211> LENGTH: 105
<212> TYPE: PRT
<213> ORGANISM: Mycobacterium abscessus

<400> SEQUENCE: 11

```
Met Ser Val Val Lys Ile Asn Ala Ile Glu Ile Pro Glu Gly Ala Gly
1               5                   10                  15

Pro Glu Leu Glu Lys Arg Phe Ala His Arg Ala Gly Ala Val Glu Asn
```

```
                        20                  25                  30
Gln Pro Gly Phe Leu Gly Phe Gln Leu Leu Arg Pro Val Lys Gly Glu
            35                  40                  45

Asp Arg Tyr Phe Val Val Thr Gln Trp Glu Ser Glu Glu Ala Phe Gln
        50                  55                  60

Ala Trp Ala Thr Gly Pro Ala Val Glu Ala His Ala Gly Gln Gln Ala
 65                  70                  75                  80

Lys Pro Val Ala Thr Gly Ala His Leu Leu Glu Phe Glu Val Val Leu
                85                  90                  95

Asp Val Thr Gly Ala Ala Ala Lys Ala
            100                 105

<210> SEQ ID NO 12
<211> LENGTH: 107
<212> TYPE: PRT
<213> ORGANISM: Bacillus cereus

<400> SEQUENCE: 12

Met Ile Ile Val Thr Asn Thr Ala Lys Ile Thr Lys Gly Asn Gly His
 1               5                  10                  15

Lys Leu Ile Glu Arg Phe Asn Lys Val Gly Gln Val Glu Thr Met Pro
                20                  25                  30

Gly Phe Leu Gly Leu Glu Val Leu Leu Thr Gln Asn Thr Val Asp Tyr
            35                  40                  45

Asp Glu Val Thr Ile Ser Thr Arg Trp Asn Ala Lys Glu Asp Phe Gln
        50                  55                  60

Gly Trp Thr Lys Ser Ser Ala Phe Lys Asp Ala His Ser His Gln Gly
 65                  70                  75                  80

Gly Met Pro Glu Tyr Ile Leu Asp Asn Lys Ile Thr Tyr Tyr Asn Val
                85                  90                  95

Glu Val Val Arg Met Pro Met Ala Ala Ala Gln
            100                 105

<210> SEQ ID NO 13
<211> LENGTH: 20
<212> TYPE: DNA
<213> ORGANISM: Artificial Sequence
<220> FEATURE:
<223> OTHER INFORMATION: Forward primer to T7 promoter

<400> SEQUENCE: 13
taatacgact cactataggg                                          20

<210> SEQ ID NO 14
<211> LENGTH: 19
<212> TYPE: DNA
<213> ORGANISM: Artificial Sequence
<220> FEATURE:
<223> OTHER INFORMATION: Reverse primer to terminator

<400> SEQUENCE: 14
gctagttatt gctcagcgg                                           19
```

BIOLOGICAL UPGRADING OF HYDROCARBON STREAMS WITH OXYGENASES

CROSS-REFERENCE TO RELATED APPLICATIONS

This application claims priority to U.S. Provisional Application No. 62/597,502 filed Dec. 12, 2017 which is herein incorporated by reference in its entirety. This application is related to two other U.S. provisional applications filed on Dec. 12, 2017: U.S. Provisional Application Nos. 62/597,488 and 62/597,512, each of which is herein incorporated by reference in its entirety.

REFERENCE TO A SEQUENCE LISTING

This application contains references to amino acid sequences and/or nucleic acid sequences which have been submitted concurrently herewith as the sequence listing text file entitled "62067233_1.txt", file size 19 KiloBytes (KB), created on 19 Sep. 2017. The aforementioned sequence listing is hereby incorporated by reference in its entirety pursuant to 37 C.F.R. § 1.52(e)(5).

FIELD

The present disclosure relates to oxygenases and methods for upgrading hydrocarbon streams, for example, crude oil.

BACKGROUND

This section provides background information related to the present disclosure. The references cited in this section are not necessarily prior art.

Typically, any number of hydrocarbon streams, such as whole crude, diesel, hydrotreated oils, atmospheric gas oils, vacuum gas oils, coker gas oils, atmospheric and vacuum residues etc., may require removal of heteroatom species, such as nitrogen-containing and/or sulfur-containing species. In particular, increasing supplies of crude oils with higher nitrogen and sulfur content paired with increasing regulations on sulfur content of refined products has resulted in the need for additional means of heteroatom removal. Catalytic hydrotreating and/or adsorption can be used to lower content of nitrogen-containing and/or or sulfur-containing species from hydrocarbon feeds. However, nitrogen-containing species can poison the hydrotreating catalysts. Thus, high pressure and high temperature hydrotreating is necessary to overcome nitrogen poisoning of the catalysts and to effectively remove the sulfur-containing species to meet sulfur content specifications of the various feeds, which can result in increased costs and emissions from refineries.

Hydrocarbon streams can also include various metal species, such as vanadium and nickel, which require removal because the presence of such metals can be detrimental to refining processes. For example, metals can be particularly damaging to catalytic cracking and catalytic hydrogenation units as they can be deposited on the catalysts rendering them inactive. Nickel and vanadium, which can be abundantly found in crude oil, can be the most damaging during catalytic refining processes. However, nickel and vanadium can be very difficult to remove as they most commonly exist as oil-soluble metalloporphyrins. Chemical, thermal and physical methods have traditionally been used for metals removal. Some chemical methods include use of a demetallization agent complexation and acid treatments (sulfuric, hydrofluoric, hydrochloric). Some thermal methods include visbreaking, coking, and hydrogenation and favored physical methods include distillation and solvent extraction. Unfortunately, these methods have inherent limitations. For example, chemical and thermal processing can require severe operating conditions, cause extensive side reactions, introduce product contamination, generate lower value products, and consume energy and fuel. With regard to physical methods, distillation alone can be non-selective, fail to provide complete metals removal, and solvent extraction can decrease the yield of desired hydrocarbon.

Thus, there is a need for improved methods for selectively removing impurities, such as heteroatoms and metals. Especially needed are methods which can remove heteroatoms and/or metals from hydrocarbons that leave the hydrocarbon backbone untouched, unlike some adsorption techniques. Removal of the entire hydrocarbon molecules is undesirable because up to 10 wt % of some crudes can contain heteroatoms and a 10 wt % loss of hydrocarbons is not economically feasible.

U.S. 2016/0333307 to Fong et al. reports using hydrogen sulfide:NADP+oxidoreductase, hydrogen sulfide:ferredoxin oxidoreductase, sulfide:flavocytochrome-c oxidoreductase, sulfide:quinone oxidoreductase, sulfur dioxygenase, sulfite oxidase, or combinations thereof to remove sulfur from fuel.

U.S. 2016/0160105 to Dhulipala et al. reports sulfhydrylases or cysteine synthases added to fuels—including fuel wells—to remove sulfur.

U.S. 2011/0089083 to Paul et al. reports using globins, peroxidases, pyrrolases, and cytochromes to remove metals from fuel.

U.S. Pat. No. 5,624,844 to Xu et al. reports using oxygenases to remove metals from fuel.

WO 2008/058165 reports immobilizing enzymes on substrates for use in catalyzing chemical reactions.

D'Antonio & Ghiladi (2008) report in an abstract from the 60$^{th}$ Southeast Regional Meeting of the American Chemical Society that oxygenases might be used to demetallize petroporphyrins in crude oil.

SUMMARY

This section provides a general summary of the disclosure, and is not a comprehensive disclosure of its full scope or all of its features.

The present disclosure provides oxygenases, for example having at least 40% sequence identity to any one or more of SEQ ID NOs: 1-12, to upgrade the quality of hydrocarbon streams. Compositions comprising an oxygenase for upgrading hydrocarbon streams are also provided herein.

Also disclosed herein are recombinant or modified oxygenase enzymes, in which the enzyme has been made more hydrophobic than its native counterpart. In certain embodiments, the oxygenase is hydrophobically modified to be at least 10% more enriched in hydrophobic amino acids selected from the group consisting of Ala, Gly, Ile, Leu, Met, Pro, Phe, and Trp. In certain embodiments, additional hydrophobic amino acids are added to the enzyme. In certain embodiments, amino acids with polar or charged side chains are replaced with hydrophobic amino acids. In certain embodiments the oxygenase is treated chemically (e.g., oxygenase is rinsed with n-propanol, oxygenase is conjugated to a polyethylene glycol, or disulfide bridges are added to the oxygenase) to be more hydrophobic.

Also disclosed herein are methods of biologically upgrading hydrocarbon streams, such as crude oil. These methods involve contacting the hydrocarbon stream with an enzyme and/or composition described herein. In certain embodiments, the contacting occurs while the hydrocarbon streams are moved through pipes or stored in reservoirs or tanks. In certain embodiments, the contacting occurs while the hydrocarbon streams are present in a reactor. In certain embodiments, the contacting occurs before the hydrocarbon stream, e.g., crude oil, may be extracted from the earth, for example by sending the enzymes and/or compositions described herein into a petroleum well. In certain embodiments, the contacting results in the removal of impurities (e.g., metal, heteroatoms, and/or asphaltenes) from the hydrocarbon stream. In additional or alternative embodiments, the contacting results in a reduction of multi-ring aromatics in the hydrocarbon stream.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and not all possible implementations. The drawings and their corresponding descriptions are not intended to limit the scope of the present disclosure.

FIG. 1 shows UV-VIS absorbance spectra for: (1A) hemin; (1B) Ni(II)-protoporphyrin (IX); (1C) Fe(III)-meso-tetra-(4-carboxyphenyl) porphine chloride; (1D) Ni(II)-meso-tetra-(4-carboxyphenyl) porphine; (1E) Ni(II)-meso-tetra-(N-methyl-4-pyridyl) porphine tetrachloride; and (1F) VO-meso-tetra-(N-methyl-4-pyridyl) porphine tetrachloride upon treatment with crude and purified HmuO. HmuO treated samples are shown at 0 hr (solid gray line) and 24 hr (dashed gray line). pET28b empty vector crude protein lysate treated samples are shown at 0 hr (solid black line) and 24 hr (dashed black line).

FIG. 2 shows UV-VIS absorbance spectra for: (2A) hemin; (2B) Ni(II)-protoporphyrin (IX); (2C) Fe(III)-meso-tetra-(4-carboxyphenyl) porphine chloride; and (2D) Ni(II)-meso-tetra-(4-carboxyphenyl) porphine upon treatment with crude and purified PigA. PigA treated samples are shown at 0 hr (solid gray line) and 24 hr (dashed gray line). pET28b empty vector crude protein lysate treated samples are shown at 0 hr (solid black line) and 24 hr (dashed black line).

FIG. 3 shows UV-VIS absorbance spectra for: (3A) hemin; (3B) Ni(II)-protoporphyrin (IX); (3C) Fe(III)-meso-tetra-(4-carboxyphenyl) porphine chloride; and (3D) Ni(II)-meso-tetra-(4-carboxyphenyl) porphine upon treatment with crude and purified HugZ. HugZ treated samples are shown at 0 hr (solid gray line) and 24 hr (dashed gray line). pET28b empty vector crude protein lysate treated samples are shown at 0 hr (solid black line) and 24 hr (dashed black line).

FIG. 4 shows UV-VIS absorbance spectra for: (4A) hemin; (4B) Ni(II)-protoporphyrin (IX); (4C) Fe(III)-meso-tetra-(4-carboxyphenyl) porphine chloride; (4D) Ni(II)-meso-tetra-(4-carboxyphenyl) porphine; (4E) Ni(II)-meso-tetra-(N-methyl-4-pyridyl) porphine tetrachloride; and (4F) VO-meso-tetra-(N-methyl-4-pyridyl) porphine tetrachloride upon treatment with crude and purified ChuS. ChuS treated samples are shown at 0 hr (solid gray line) and 24 hr (dashed gray line). pET28b empty vector crude protein lysate treated samples are shown at 0 hr (solid black line) and 24 hr (dashed black line).

FIG. 5 shows UV-VIS absorbance spectra for: (5A) hemin; (5B) Ni(II)-protoporphyrin (IX); (5C) Fe(III)-meso-tetra-(4-carboxyphenyl) porphine chloride; and (5D) Ni(II)-meso-tetra-(4-carboxyphenyl) porphine upon treatment with crude and purified IsdI. IsdI treated samples are shown at 0 hr (solid gray line) and 24 hr (dashed gray line). pET28b empty vector crude protein lysate treated samples are shown at 0 hr (solid black line) and 24 hr (dashed black line).

FIG. 6 shows UV-VIS absorbance spectra for: (6A) hemin; (6B) Ni(II)-protoporphyrin (IX); (6C) Fe(III)-meso-tetra-(4-carboxyphenyl) porphine chloride; and (6D) Ni(II)-meso-tetra-(4-carboxyphenyl) porphine upon treatment with crude and purified IsdG. IsdG treated samples are shown at 0 hr (solid gray line) and 24 hr (dashed gray line). pET28b empty vector crude protein lysate treated samples are shown at 0 hr (solid black line) and 24 hr (dashed black line).

DETAILED DESCRIPTION

Unless defined otherwise, all technical and scientific terms used herein have the same meaning as commonly understood by one of ordinary skill in the art to which this invention belongs. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference. In case of conflict between definitions incorporated by reference and definitions set out in the present disclosure, the definitions of the present disclosure will control.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

Definitions

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B," "A or B," "A," and "B."

As used herein, and unless otherwise specified, the term "Cn" means hydrocarbon(s) having n carbon atom(s) per molecule, wherein n is a positive integer.

As used herein, the term "hydrocarbon(s)" means a class of compounds containing hydrogen bound to carbon, which may be linear, branched or cyclic, and encompasses (i) saturated hydrocarbon compounds, (ii) unsaturated hydrocarbon compounds, and (iii) mixtures of hydrocarbon compounds (saturated and/or unsaturated) including mixtures of hydrocarbon compounds having different values of n. The term "hydrocarbon(s)" is also intended to encompass hydrocarbons containing one or more heteroatoms, such as, but not limited to nitrogen, sulfur, and oxygen, and/or containing one or more metals, such as vanadium and nickel. Non-limiting examples of heteroatom-containing and metal-containing hydrocarbons include porphyrins or petroporphyrins, and metalloporphyrins. The term "porphyrin" refers to a cyclic structure typically composed of four modified pyrrole rings interconnected at their a carbon atoms via methane bridges (=C—) and having two replaceable hydrogens on two nitrogens, where, for example, various metal atoms can be substituted to form a metalloporphyrin. Examples of nitrogen-containing species include, but are not limited to carbazoles, imidazoles, pyrroles, quinones, quinilines and combinations thereof. Examples of sulfur-containing species include, but are not limited to mercaptans, thiols, disulfides, thiophenes, benzothiophenes, dibenzothiophenes and combinations thereof. Examples of oxygen-containing species include, but are not limited to furans, indoles, carbazoles, benzcarbazoles, pyridines, quinolines, phenanthridines, hydroxypyridines, hydroxyquinolines, dibenzofuranes, naphthobenzofuranes, phenols, aliphatic ketones, carboxylic acids, and sulfoxides.

As used herein, the term "hydrocarbon stream" refers to any stream comprising hydrocarbons, while "hydrocarbon composition" refers to any composition comprising hydrocarbons. These hydrocarbons may be present in the oil reservoir/wellbore, pipes, tanks, reactors, etc. Examples of hydrocarbon streams or compositions include, but are not limited to hydrocarbon fluids, whole crude oil, diesel, kerosene, virgin diesel, light gas oil (LGO), lubricating oil feedstreams, heavy coker gasoil (HKGO), de-asphalted oil (DAO), fluid catalytic cracking (FCC) main column bottom (MCB), steam cracker tar, streams derived from crude oils, shale oils and tar sands, streams derived from the Fischer-Tropsch processes, reduced crudes, hydrocrackates, raffinates, hydrotreated oils, atmospheric gas oils, vacuum gas oils, coker gas oils, atmospheric and vacuum residues (vacuum resid), deasphalted oils, slack waxes and Fischer-Tropsch wax. The hydrocarbon streams may be derived from various refinery units, such as, but not limited to distillation towers (atmospheric and vacuum), hydrocrackers, hydrotreaters and solvent extraction units.

As used herein, the term "asphaltene" refers to a class of hydrocarbons, present in various hydrocarbon streams, such as crude oil, bitumen, or coal, that are soluble in toluene, xylene, and benzene, yet insoluble in paraffinic solvents, such as n-alkanes, e.g., n-heptane and n-pentane. Asphaltenes may be generally characterized by fused ring aromaticity with some small aliphatic side chains, and typically some polar heteroatom-containing functional groups, e.g., carboxylic acids, carbonyl, phenol, pyrroles, and pyridines, capable of donating or accepting protons intermolecularly and/or intramolecularly. Asphaltenes may be characterized as a high molecular weight fraction of crude oils, e.g., an average molecular weight (about 1000 and up to 5,000) and very broad molecular weight distribution (up to 10,000), and high coking tendency.

As used herein, the term "upgrade" or "upgrading" generally means to improve quality and/or properties of a hydrocarbon stream and is meant to include physical and/or chemical changes to a hydrocarbon stream. Further, upgrading is intended to encompass removing impurities (e.g., heteroatoms, metals, asphaltenes, etc.) from a hydrocarbon stream, converting a portion of hydrocarbons into shorter chain length hydrocarbons, cleaving single ring or multi-ring aromatic compounds present in a hydrocarbon stream, and/or reducing viscosity of a hydrocarbon stream.

As used herein, the term "hydrophobic" refers to a substance or a moiety, which lacks an affinity for water. That is, a hydrophobic substance or moiety tends to substantially repel water, is substantially insoluble in water, does not substantially mix with or be wetted by water or to do so only to a very limited degree and/or does not absorb water or, again, to do so only to a very limited degree.

The term "heterologous" with regard to a gene regulatory sequence (such as, for example, a promoter) means that the regulatory sequence or is from a different source than the nucleic acid sequence (e.g., protein coding sequence) with which it is juxtaposed in a nucleic acid construct. By way of non-limiting example, a slyD gene from $E.\ coli$ is heterologous to a slyD promoter from $Y.\ pestis$. Similarly, the slyD gene is heterologous to the hypB promoter, even when both slyD and hypB are from $E.\ coli$.

The term "expression cassette," as used herein, refers to a nucleic acid construct that encodes a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

The term "operably linked," as used herein, denotes a configuration in which a control sequence is placed at an appropriate position relative to the coding sequence of a polynucleotide sequence such that the control sequence directs the expression of the coding sequence of a polypeptide and/or functional RNA). Thus, a promoter is in operable linkage with a nucleic acid sequence if it can mediate transcription of the nucleic acid sequence. When introduced into a host cell, an expression cassette can result in transcription and/or translation of an encoded RNA or polypeptide under appropriate conditions. Antisense or sense constructs that are not or cannot be translated are not excluded by this definition. In the case of both expression of transgenes and suppression of endogenous genes (e.g., by antisense, or sense suppression) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

"Naturally-occurring" and "wild-type" (WT) refer to a form found in nature. For example, a naturally occurring or wild-type nucleic acid molecule, nucleotide sequence, or protein may be present in, and isolated from, a natural source, and is not intentionally modified by human manipulation.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity can be determined by various computer programs for aligning the sequences to be compared based on designated program parameters. For example, sequences can be aligned and compared using the local homology algorithm of Smith & Waterman (1981) Adv. Appl. Math. 2:482-89, the homology alignment algorithm of Needleman & Wunsch (1970) J. Mol. Biol. 48:443-53, or the search for similarity method of Pearson & Lipman (1988) Proc. Nat'l. Acad. Sci. USA 85:2444-48, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al. (1990) *J. Mol. Biol.* 215:403-10, is publicly available through software provided by the National Center for Biotechnology Information (at the web address www.ncbi.nlm.nih.gov). This algorithm identifies high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=-4; and a comparison of both strands. The TBLASTN program (using a protein sequence to query nucleotide sequence databases) uses as defaults a word length (W) of 3, an expectation (E) of 10, and a BLOSUM 62 scoring matrix. See, Henikoff & Henikoff (1992) *Proc. Nat'l. Acad. Sci. USA* 89:10915-19.

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

"Pfam" is a large collection of protein domains and protein families maintained by the Pfam Consortium and available at several sponsored World Wide Web sites. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment, whereas Pfam-B families are generated automatically from the non-redundant clusters of the latest release of the Automated Domain Decomposition algorithm (ADDA; Heger A, Holm L (2003) *J Mol Biol* 328(3):749-67). All identified sequences belonging to the family are then used to automatically generate a full alignment for the family (Sonnhammer et al. (1998) *Nucleic Acids Research* 26: 320-322; Bateman et al. (2000) *Nucleic Acids Research* 26: 263-266; Bateman et al. (2004) *Nucleic Acids Research* 32, Database Issue: D138-D141; Finn et al. (2006) *Nucleic Acids Research Database Issue* 34: D247-251; Finn et al. (2010) *Nucleic Acids Research Database Issue* 38: D211-222).

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. et al., (1979) Principles of Protein Structure, Springer-Verlag). According to such analyses, groups of amino acids can be defined where amino acids within a group exchange preferentially with each other, and therefore resemble each other most in their impact on the overall protein structure (Schulz, G. E. et al., (1979) Principles of Protein Structure, Springer-Verlag). Examples of amino acid groups defined in this manner include an "aromatic or cyclic group," including Pro, Phe, Tyr, and Trp. Within each group, subgroups can also be identified. For example, the group of charged amino acids can be sub-divided into sub-groups including: the "positively-charged sub-group," comprising Lys, Arg and His; and the "negatively-charged sub-group," comprising Glu and Asp. In another example, the aromatic or cyclic group can be sub-divided into sub-groups including: the "nitrogen ring sub-group," comprising Pro, His, and Trp; and the "phenyl sub-group" comprising Phe and Tyr. In another further example, the hydrophobic group can be sub-divided into sub-groups including: the "large aliphatic non-polar sub-group," comprising Val, Leu, and Ile; the "aliphatic slightly-polar sub-group," comprising Met, Ser, Thr, and Cys; and the "small-residue sub-group," comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn such that a free —NH$_2$ can be maintained.

Oxygenases

As disclosed herein, enzyme class oxygenases can be used to upgrade hydrocarbon streams by removing heteroatoms and cleaving multi-ring aromatic structures. By contacting a hydrocarbon stream (e.g., crude oil) with the oxygenase, impurities such as, heteroatoms, metals, and asphaltenes can be removed and properties of the hydrocarbon stream can be improved, for example, viscosity may be lowered. Additionally, the fraction of the upgraded product that is recoverable can be increased. In certain embodiments, the oxygenase is capable of cleaving heteroatom-carbon bonds (e.g., nitrogen-carbon bonds, sulfur-carbon bonds) and carbon-carbon bonds in non-porphyrin compounds. Examples of non-porphyrin compounds include, but are not limited to pyridine, pyrrole, indole, acridine, carbazole, dibenzothiophene, dibenzofuran, fluorene, phenanthrene, anthracene, tetracene, chrysene, triphenylene, pyrene, pentacene, benzo(a)pyrene, corannulene, benzo(ghi)perylene, coronene, ovalene, benzo(c)fluorine, other polyaromatic hydrocarbons, and any of the listed compounds with substitutions.

In certain embodiments, the oxygenase can be an oxygenase that classifies as belonging to Pfam family PF01126. Although the enzyme(s) can be present in the context of a host cell (e.g., a microbial cell), in certain embodiments the enzymes are substantially free or even totally free of cells, cell components, or cellular debris beyond the bare enzyme itself.

In some embodiments, the oxygenase may be thermally stable from about 15° C. to about 150° C., about 50° C. to about 120° C. or about 90° C. to about 120° C.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:1.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:2.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:3.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:4.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:5.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:6.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:7.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:8.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:9.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:10.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:11.

In certain embodiments, the oxygenase has at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) sequence identity to SEQ ID NO:12.

Hydrophobic Modification

In certain embodiments, oxygenases as described herein can be modified to become more hydrophobic. Because the hydrocarbon stream may be a hydrophobic environment, by making the enzyme (in particular those enzyme surfaces that are exposed to the hydrophobic environment of the hydrocarbon stream) more hydrophobic, the enzyme can be better able to tolerate the stresses of the environment.

In certain embodiments, the oxygenase can be modified to be more hydrophobic by the inclusion of a greater number of hydrophobic amino acids (Ala, Gly, Ile, Leu, Met, Pro, Phe, and Trp) in the enzyme's primary sequence. This can be accomplished in a number of different ways, none of which are mutually exclusive of each other. For example, one can replace a given polar (Asn, Cys, Gln, Ser, Thr, and Tyr) or charged (Arg, Asp, Glu, His, and Lys) with a hydrophobic amino acid. Additionally or alternatively, one can add one or more additional hydrophobic amino acid between two amino acids already present in the primary sequence of the wild type. Additionally or alternatively, one can add one or more (e.g., at least 5, at least 10, at least 20, at least 30, at least 40, or at least 50) additional hydrophobic amino acids at the amino and/or carboxy terminus of the enzyme. The result of these additions and/or substitutions can result in an enzyme that is at least 5% (e.g., at least 10%, at least 15%, at least 20%, at least 25%, at least 30%, at least 35%, at least 40%, at least 45%, or at least 50%) more hydrophobic than the corresponding wild-type enzyme sequence.

In order for an enzyme's amino acid sequence to be modified relative to the corresponding wild type sequence, the modified sequence must be less than 100% identical to its corresponding wild type sequence. In certain embodiments, the modified enzyme is no more than about 95% identical to the corresponding wild type, for example no more than about 90%, no more than about 85%, no more than about 80%, no more than about 75%, no more than about 70%, no more than about 65%, or no more than about 70% identical. However, the modified enzyme will still be at least about 40% (for example, at least 50%, at least 60%, at least 70%, at least 80%, at least 90%, at least 91%, at least 92%, at least 93%,or at least 94%) identical to the corresponding wild type sequence (e.g., a sequence selected from the group consisting of SEQ ID NOs: 1-12).

Additionally or alternatively, in certain embodiments an oxygenase can be made more hydrophobic by chemical modification. In certain embodiments, the enzyme can be rinsed with n-propanol. In certain embodiments polyethylene glycol can be conjugated to the oxygenase. In certain embodiments, disulfide bridges can be added to the oxygenase. The addition of disulfide bridges can affect the enzyme's tertiary structure. Therefore, additional disulfide bridges must be placed carefully. The person of ordinary skill knows how to place disulfide bridges in a manner that will cause minimal disruption to oxygenase activity.

Nucleic Acids

Also described herein are nucleic acids encoding oxygenases for use with the methods and compositions described herein. The person of ordinary skill knows that the degeneracy of the genetic code permits a great deal of variation among nucleotides that all encode the same protein. For this reason, it is to be understood that the representative nucleotide sequences disclosed herein are not intended to limit the understanding of phrases such as "a nucleotide encoding a protein having at least 70% identity to SEQ ID NO . . . " or "a construct encoding SEQ ID NO . . . ".

In certain embodiments, the nucleotide encodes an oxygenase having at least 40% (for example, at least 50%, at least 60%, at least 70%, at least 80%, at least 90%, at least 91%, at least 92%, at least 93%, at least 94%, at least 95%, at least 96%, at least 97%, at least 98%, or at least 99%) identity to a sequence selected from the group consisting of SEQ ID NOs:1-12. In certain embodiments, the nucleotide is selected from the group consisting of SEQ ID NOs:1-3, 6, & 9.

In certain embodiments, the nucleotides disclosed herein are incorporated into expression cassettes. The choice of regulator elements such as promoter or terminator or splice site for use in expression cassettes depends on the intended cellular host for gene expression. The person of ordinary skill knows how to select regulatory elements appropriate for an intended cellular host. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in both directions off of opposite strands). A promoter may be a constitutive promoter, a repressible promoter, or an inducible promoter. Non-limiting examples of promoters include, for example, the T7 promoter, the cytomegalovirus (CMV) promoter, the SV40 promoter, and the RSV promoter. Examples of inducible promoters include the lac promoter, the pBAD (araA) promoter, the Tet promoter (U.S. Pat. Nos. 5,464,758 and 5,814,618), and the Ecdysone promoter (No et al. (1996) *Proc. Natl. Acad. Sci.* 93:3346-51).

In certain embodiments, the nucleotides and/or expression cassettes disclosed herein can be incorporated into vectors. A vector can be a nucleic acid that has been generated via human intervention, including by recombinant means and/or direct chemical synthesis, and can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism. A vector can be an expression vector that includes one or more specified nucleic acid "expression control elements" that permit transcription and/or translation of a particular nucleic acid in a host cell. The vector can be a plasmid, a part of a plasmid, a viral construct, a nucleic acid fragment, or the like, or a combination thereof.

In certain embodiments the nucleotide coding sequences may be revised to produce messenger RNA (mRNA) with codons preferentially used by the host cell to be transformed ("codon optimization"). Thus, for enhanced expression of transgenes, the codon usage of the transgene can be matched with the specific codon bias of the organism in which the transgene is desired to be expressed. The precise mechanisms underlying this effect are believed to be many, but can include the proper balancing of available aminoacylated tRNA pools with proteins being synthesized in the cell, coupled with more efficient translation of the transgenic mRNA when this need is met. In some examples, only a portion of the codons is changed to reflect a preferred codon usage of a host microorganism. In certain examples, one or more codons are changed to codons that are not necessarily the most preferred codon of the host microorganism encoding a particular amino acid. Additional information for codon optimization is available, e.g. at the codon usage database of GenBank. The coding sequences may be codon optimized for optimal production of a desired product in the host organism selected for expression. In certain examples, the nucleic acid sequence(s) encoding an oxygenase are codon optimized for expression in *E. coli*. In some aspects, the nucleic acid molecules of the invention encode fusion proteins that comprise an enzyme (e.g., an oxygenase). For example, the nucleic acids of the invention may comprise polynucleotide sequences that encode glutathione-S-transferase (GST) or a portion thereof, thioredoxin or a portion thereof, maltose binding protein or a portion thereof, polyhistidine (e.g. His6), poly-HN, poly-lysine, a hemagglutinin tag sequence, HSV-Tag, and/or at least a portion of HIV-Tat fused to the enzyme-encoding sequence.

The vector can be a high copy number vector, a shuttle vector that can replicate in more than one species of cell, an expression vector, an integration vector, or a combination thereof. Typically, the expression vector can include a nucleic acid comprising a gene of interest operably linked to a promoter in an expression cassette, which can also include, but is not limited to, a localization peptide encoding sequence, a transcriptional terminator, a ribosome binding site, a splice site or splicing recognition sequence, an intron, an enhancer, a polyadenylation signal, an internal ribosome entry site, and similar elements.

Expression in Host Cells

In a further aspect, a recombinant microorganism or host cell, such as a recombinant *E. coli*, comprising a non-native gene encoding an oxygenase is disclosed herein. In certain embodiments, the oxygenase comprises an amino acid sequence having at least about 40% sequence identity to a sequence selected from the group consisting of SEQ ID NOs:1-12, and/or to an active fragment of any thereof. For example, the non-native gene can encode an oxygenase having an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a sequence selected from the group consisting of SEQ ID NOs:1-12. In certain embodiments, the sequence having at least about 40% identity to a sequence selected from the group consisting of SEQ ID NOs:1-12 is modified as described herein to make the resulting protein more hydrophobic than its wild-type counterpart.

In certain embodiments, the host cell can be a prokaryotic host cell, either gram negative or gram positive. By way of non-limiting example, the host cell can be an *E. coli* host cell. The skilled artisan is familiar with the media and techniques necessary for the culture of prokaryotic host cells, including *E. coli*.

In certain embodiments, the host cell can be a eukaryotic host cell, such as a yeast (e.g., *S. cerevisiae* or *S. pombe*) or an insect cell (e.g., a *Spodoptera frugiperda* cell such as Sf9 or Sf21). The skilled artisan is familiar with the media and techniques necessary for the culture of eukaryotic host cells, including yeast and insect cells.

Compositions

Also disclosed herein are compositions comprising one or more oxygenases. The compositions are useful for upgrading hydrocarbon streams as discussed herein. In addition to one or more oxygenases (e.g. two, three or four oxygenases), the compositions may also include other enzymes useful for upgrading hydrocarbon streams, such as a dioxygenase, a ferredoxin, ferredoxin reductase, a nickel-binding protein or a combination thereof.

In addition to comprising other enzymes, a composition herein can comprise one or more of a lubricant, a surfactant, a viscosity additive, a fluid loss additive, a foam control agent, a weighting material, and a salt.

Methods of Use

Also provided herein are methods of using the oxygenases and compositions described herein. In various aspects, methods of biologically upgrading a hydrocarbon stream are provided herein comprising contacting the hydrocarbon stream with an oxygenase and/or a composition described herein. In some embodiments, the upgrading can comprise removing at least a portion of impurities from the hydrocarbon stream. Exemplary impurities include, but are not limited to heteroatoms (e.g., nitrogen and/or sulfur), metals (e.g., nickel and/or vanadium), asphaltenes, and a combination thereof. In a particular embodiment, methods of removing heteroatoms from a hydrocarbon stream are provided herein comprising contacting the hydrocarbon stream with an oxygenase and/or composition described herein.

In some embodiments, the oxygenase may be capable of cleaving heteroatom-carbon bonds (e.g., nitrogen-carbon bonds, sulfur-carbon bonds) and/or carbon-carbon bonds, particularly, in non-porphyrin compounds (as mentioned above), to release the impurities. It is contemplated herein that removal of impurities from the hydrocarbon stream also encompasses conversion of larger hydrocarbon compounds to smaller hydrocarbon compounds, which can also advantageously reduce viscosity of the hydrocarbon stream, as well as conversion of heteroatom containing compounds into compounds which can be more easily removed in further upgrading or refining processes, such as hydrotreating.

For example, with respect to asphaltenes, removal of asphaltenes may be accomplished by an oxygenase described herein cleaving the multi-ring aromatics present in the asphaltenes, such that the asphaltenes are converted into smaller hydrocarbons thereby reducing asphaltene content (e.g., multi-ring aromatic content) in the hydrocarbon stream. For example, an oxygenase described herein may be capable of converting larger nitrogen containing compounds into smaller nitrogen containing compounds, such as amines, which can be more easily removed in further upgrading or refining processes, such as hydrotreating. In some embodiments, methods of reducing content of multi-ring aromatic molecules in a hydrocarbon stream are provided herein comprising contacting the hydrocarbon stream with an oxygenase and/or composition described herein.

In other embodiments, the upgrading methods described herein can enhance the quantity of hydrocarbons recovered from a hydrocarbon stream or limit the loss of hydrocarbons, for example, an oxygenase described herein can selectively remove impurities from hydrocarbon compounds in the hydrocarbon stream without removing the entire hydrocarbon molecules, i.e., leaving the hydrocarbon backbone substantially untouched. Thus, in some embodiments, there can be lower loss of hydrocarbons following separation of the impurities from the hydrocarbon stream, for example, a loss of ≤15 wt %, ≤10 wt %, ≤8.0 wt %, ≤5.0 wt %, or ≤1.0 wt % of hydrocarbons may occur after separation of the impurities from the hydrocarbon stream.

Many of the enzymes described herein require a reducing agent (e.g., NADPH) co-factor to function. In certain embodiments, the enzymes make contact with the hydrocarbon stream in the presence of a reducing agent. In certain embodiments, the enzymes make contact with the hydrocarbon stream without the addition of reducing agents. Where a reducing agent is not added, the reducing power necessary for enzyme function can be supplied in some other manner, for example by passing a low power current through the environment while the enzymes are in contact with the hydrocarbon stream.

The hydrocarbon stream may be contacted with an oxygenase and composition described herein for any suitable amount of time. Advantageously, upgrading of the hydrocarbon stream when contacted with the oxygenases described herein may occur in a short period of time, for example, the hydrocarbon stream may be contacted with oxygenases for ≤about 10 hours, ≤about 5.0 hours, ≤about 1.0 hours, ≤about 30 minutes, ≤about 10 minutes, ≤about 1.0 minutes, ≤about 30 seconds, ≤about 10 seconds or ≤about 1.0 second.

Advantageously, the methods described here can be performed across a wide range of pressures and temperatures and even at ambient pressure and temperature. Effective upgrading conditions can include temperatures of about 15° C. to about 30° C. and pressures of from about 90 kPa to about 200 kPa. Additionally or alternatively, upgrading can be performed at higher temperatures of about 30° C. to about 200° C. or 30° C. to about 120° C.

Locations, Forms and Immobilization

The methods described herein can be performed in various locations. For example, the oxygenase may be present in an oil reservoir/wellbore, a pipeline, a tank, a vessel, a reactor, or any combination thereof. In a particular embodiment, the oxygenase may contact crude oil in the oil reservoir/wellbore, for example, through enzyme injection into the oil reservoir/wellbore. In another particular embodiment, the oxygenase may contact a hydrocarbon stream, e.g., crude oil or hydrocarbon product stream, as it flows and/or resides in a pipeline and/or a holding vessel or a tank. When added to a pipeline and/or a holding vessel or a tank, a hydrocarbon stream may be upgraded without any substantially additional processing time, for example, when a hydrocarbon stream is awaiting further processing and/or transport.

In certain embodiments, the oxygenases and compositions can be present in free form or crystal form, while in other embodiments the oxygenases and compositions can be immobilized on a carrier or scaffold, such as a membrane, a filter, a matrix, diatomaceous material, particles, beads, in an ionic liquid coating, an electrode, or a mesh.

In certain embodiments, the oxygenases and compositions can be present in crystal form and the crystals can be added to hydrocarbon streams at the various locations listed above. Standard techniques known to a person of ordinary skill in the art may be used to form oxygenase crystals.

Additionally or alternatively, the oxygenases and compositions can be immobilized by standard techniques known to a person of ordinary skill in the art, and the hydrocarbon stream may contact an immobilized oxygenase by flowing over, through, and/or around the immobilized oxygenase. Suitable carriers or scaffolds include, but are not limited to a membrane, a filter, a matrix, diatomaceous material, particles, beads, an ionic liquid coating, an electrode, a mesh, and a combination thereof. In some embodiments, the matrix may comprise an ion-exchange resin, a polymeric resin and/or a water-wet protein attached to a hydrophilic surface, being a surface that is capable of forming an ionic or hydrogen bond with water and has a water contact angle of less than 90 degrees. For example, one or more oxygenases may be present on a matrix with a thin layer of water-wet protein, which may maintain structure and function of the oxygenase. In some embodiments, the particles and/or beads may comprise a material selected from the group consisting of glass, ceramic, and a polymer (e.g., polyvinyl alcohol beads). In some embodiments, one or more oxygenases may be dispersed into heated and melted ionic liquids, and following cooling, the one or more oxygenases may be coated in an ionic liquid, which may improve stability of a oxygenase, for example, when contacted with organic solvents.

Additionally or alternatively, suitable carriers or scaffolds can comprise at least one transmembrane domain (e.g., alpha helical domain including hydrophobic residues, which can lock an oxygenase within a matrix), at least one peripheral membrane domain (e.g., signal proteins), and a combination thereof along with the one or more oxygenases. In other embodiments, the oxygenase can be semi-immobilized in a packed bed of a reactor.

Optional Method Steps

Additionally or alternatively, the methods can further comprise selecting one or more oxygenases for contacting with the hydrocarbon stream based upon impurity type and content of the hydrocarbon stream. For example, the hydrocarbon stream may be tested to determine impurities content (e.g., nitrogen, sulfur, nickel, and vanadium content) and properties. Then an oxygenase or mixture of oxygenases may be selected based on the impurities present in the hydrocarbon stream and properties of the hydrocarbon stream. The oxygenase or mixture of oxygenases may then be obtained or produced via methods known in the art, for example, the oxygenase(s) may be produced in *Escherichia coli*, the cells may be used as whole cells or be lysed, and the soluble fraction may be removed.

In other embodiments, methods of enhanced oil recovery using one or more oxygenase as described herein are provided. For example, one or more oxygenase, singularly or in combination with an injection fluid, may be introduced to an oil reservoir/wellbore. In some embodiments, the one or more oxygenase may reduce the viscosity of the oil present in the reservoir/wellbore allowing for increased oil recovery.

It is also contemplated herein that the oxygenases described herein may be used in further refining processes, for example, the oxygenases may be present in reactors for hydroprocessing, hydrofinishing, hydrotreating, hydrocracking, catalytic dewaxing (such as hydrodewaxing), solvent dewaxing, and combinations thereof.

EMBODIMENTS

Embodiment 1

A method of removing heteroatoms from a hydrocarbon stream comprising contacting the hydrocarbon stream with an oxygenase.

Embodiment 2

A method of reducing the content of multi-ring aromatic molecules in a hydrocarbon stream, the method comprising contacting the hydrocarbon stream with an oxygenase.

Embodiment 3

The method of Embodiment 1 or 2, wherein the oxygenase is substantially cell-free.

Embodiment 4

The method of any one of the previous Embodiments, wherein the oxygenase is a recombinant enzyme.

Embodiment 5

The method of Embodiment 4, wherein the oxygenase belongs to Pfam family PF01126.

Embodiment 6

The method of any one of the previous Embodiments, wherein the oxygenase is capable of cleaving heteroatom-carbon bonds and carbon-carbon bonds in non-porphyrin compounds.

Embodiment 7

The method of any one of the previous Embodiments, wherein the oxygenase has at least 85% sequence identity to an oxygenase selected from the group consisting of SEQ ID NOs:1-12.

Embodiment 8

The method of any one of the previous Embodiments, wherein the heteroatom is nitrogen or sulfur.

Embodiment 9

The method of any one of the previous Embodiments, wherein the hydrocarbon stream is crude oil or vacuum resid.

Embodiment 10

The method of any one of the previous Embodiments, wherein the contacting is performed at a temperature from about 15° C. to about 90° C.

Embodiment 11

The method of any one of the previous Embodiments, wherein the oxygenase is thermally stable from about 90° C. to about 120° C.

Embodiment 12

The method of any one of the previous Embodiments further comprising selecting one or more oxygenases for the contacting step based upon heteroatom type or multi-ring aromatic content.

Embodiment 13

The method of any one of the previous Embodiments, wherein there is less than 10 wt % loss of hydrocarbon following heteroatom removal.

Embodiment 14

The method of any one of the previous Embodiments, wherein the oxygenase is present in an oil reservoir, a pipeline, a tank, a vessel, and/or a reactor.

Embodiment 15

The method of any one of the previous Embodiments, wherein the oxygenase is in free form, crystal form, and/or immobilized on a carrier.

Embodiment 16

The method of Embodiment 15, wherein the carrier is selected from the group consisting of a membrane, a filter, a matrix, diatomaceous material, particles, beads, an ionic liquid, and a mesh.

Embodiment 17

The method of Embodiment 16, wherein the matrix comprises a polymeric resin and/or a water wet protein.

Embodiment 18

The method of Embodiment 16, wherein the particles and/or beads comprise a material selected from the group consisting of glass, ceramic, and a polymer.

Embodiment 19

The method of any one of the previous Embodiments, wherein the oxygenase is hydrophobically modified to be at least 10% more enriched in hydrophobic amino acids selected from the group consisting of Ala, Gly, Ile, Leu, Met, Pro, Phe, and Trp.

Embodiment 20

The method of Embodiment 19, wherein the oxygenase is selected from the group consisting of SEQ ID NOs:1-12.

Embodiment 21

The method of Embodiment 19 or 20, wherein the enrichment is at least 20%.

Embodiment 22

The method of any one of Embodiments 19-21, wherein enrichment is achieved by replacing a native residue with the hydrophobic amino acid.

Embodiment 23

The method of any one of Embodiments 19-22, wherein enrichment is achieved by adding the hydrophobic amino acid between two native residues.

Embodiment 24

The method of any one of the previous Embodiments, wherein the oxygenase is rinsed with n-propanol.

Embodiment 25

The method of any one of the previous Embodiments, wherein the oxygenase is conjugated to a polyethylene glycol.

Embodiment 26

The method of any one of the previous Embodiments, wherein disulfide bridges are added to the oxygenase.

Embodiment 27

The method of any one of the previous Embodiments, wherein one to ten hydrophobic amino acid residues are added to an amino or carboxy terminus of the oxygenase, wherein the hydrophobic amino acid is selected from the group consisting of Ala, Gly, Ile, Leu, Met, Pro, Phe, and Trp.

Embodiment 28

A recombinant polypeptide having at least 70% sequence identity but no more than 90% sequence identity to a sequence selected from the group consisting of SEQ ID NOs:1-12, wherein the sequence is manipulated to be at least 10% more enriched in hydrophobic amino acids relative to the sequence selected from SEQ ID NOs:1-12, and wherein the hydrophobic amino acids are selected from the group consisting of Ala, Gly, Ile, Leu, Met, Pro, Phe, and Trp.

Embodiment 29

The recombinant polypeptide of Embodiment 28, wherein the enrichment is at least 20%.

EXAMPLES

Without further description, it is believed that one of ordinary skill in the art can, using the preceding description and the following illustrative examples, make and utilize the enzymes and compositions described herein and practice the methods disclosed herein.

To test the ideas discussed above, six oxygenases were selected (Table 1) to screen for activity against aqueous soluble model nickel- and vanadium-containing porphyrins.

TABLE 1

Oxygenase Properties

|  | HmuO | PigA | HugZ |
|---|---|---|---|
| Organism | C. jeikeium | P. aeruginosa | H. pylori |
| Monomer size (kDa) | 24 | 23 | 28 |
| Class |  | Canonical |  |
| SEQ ID NO | 1 | 2 | 5 |
| Active site | Proximal & distal helices; His axial heme ligand; Gly-rich distal helix; wider than HO | Proximal & distal helices; His axial heme ligand; Gly-rich distal helix; unusual heme seating | Flexible C-term. Loop with iron-binding, non-catalytic His; essential Arg residue |
| Products | biliverdin IX-α | β & δ biliverdin | γ biliverdin |

|  | ChuS | IsdI | IsdG |
|---|---|---|---|
| Organism | E. coli | S. aureus | S. aureus |
| Monomer size (kDa) | 21 | 12.5 | 12.8 |
| Class |  | Non-Canonical |  |
| SEQ ID NO | 3 | 6 | 9 |
| Active site | His axial heme ligand; antiparallel βsheets | β sheet & α helix; HOs His axial heme ligand absent; HOs Gly-rich distal helix absent | β sheet & α helix; HOs His axial heme ligand absent; HOs Gly-rich distal helix absent |
| Products | biliverdin | oxo-bilirubin | oxo-bilirubin |

Six model porphyrins: hemin; Ni(II)-protoporphyrin (IX); Fe(III)-meso-tetra-(4-carboxyphenyl) porphine chloride; Ni(II)-meso-tetra-(4-carboxyphenyl) porphine; Ni(II)-meso-tetra-(Nmethyl-4-pyridyl) porphine tetrachloride; & VO-meso-tetra-(N-methyl-4-pyridyl) porphine tetrachloride were chosen as test substrates for the six representative oxygenases. These substrates were chosen because Hemin was chosen as it is the molecule closest to heme, a natural oxygenase substrate, that is aqueous soluble and stable at concentrations compatible with UV-VIS absorbance spectroscopy. Ni(II)-protoporphyrin (IX) contains the same small hydrocarbon tetrapyrrole as hemin. However, hemin's central iron has been replaced with nickel. This single difference between substrates permits assessment of the role that the central metal molecule plays in enzyme binding and demetallation. All candidate enzymes were then tested against Fe(III)-meso-tetra-(4-carboxyphenyl) porphine chloride and Ni(II)-meso-tetra-(4-carboxyphenyl) porphine. Fe(III)-meso-tetra-(4-carboxyphenyl) porphine chloride differs from hemin by its R-groups. Carboxyphenyls, large, aromatic-containing, R-groups, extending from all four carbons that connect the pyrrole rings. Comparing enzyme activity between this substrate and hemin allows one to test the impacts that substrate size and R-group character have on binding and demetallation. In parallel to the two smallest model compounds, hemin and Ni(II)-protoporphyrin (IX), Ni(II)-meso-tetra-(4-carboxyphenyl) porphine is simply the nickel containing variant of Fe(III)-meso-tetra-(4-carboxyphenyl) porphine chloride. Changes in the absorbance of this substrate provide further support for the relative contribution of the central metal ion and the tetrapyrrole R-group character to enzyme-porphyrin binding and demetallation.

Testing in an aqueous environment to eliminate mass transfer limitations that occur between multiple phases and stressful non-aqueous conditions that may change protein structure and/or inhibit function. This approach minimizes false-negative results to maximize the number of potential protein candidates that can be identified.

UV-VIS spectroscopy was used for initial screening of protein activity against numerous model compounds because each model porphyrin has a characteristic UV-VIS absorbance spectrum. A shift in the wavelength of maximal absorbance, commonly referred to as the "Soret band," indicates a change in porphyrin conformation or a protein-porphyrin interaction. A decrease in absorbance—or in the magnitude of the Soret band—implicates a change in intact porphyrin concentration, potentially caused by porphyrin demetallation.

TABLE 2

Soret band wavelengths

| Porphyrin | Soret band wavelength (nm) | | | | | | |
|---|---|---|---|---|---|---|---|
|  | Control | HmuO | ChuS | HugZ | PigA | IsdI | IsdG |
| Hemin | 390 | 399 | 405/400 | 405 | 400 | 390 | 390 |
| Ni(II)-protoporphyrin (IX) | 400 | 400 | 400 | 417 | 400 | 400 | 400 |
| Fe(III)-meso-tetra-(4-carboxyphenyl) porphine chloride | 410 | 417 | 424/420 | 418 | 414 | 410 | 410 |
| Ni(II)-meso-tetra-(4-carboxyphenyl) porphine | 400 | 405 | 410/405 | 400 | 404 | 400 | 400 |
| Ni(II)-meso-tetra-(Nmethyl-4-pyridyl) porphine tetrachloride | 440 | 440 | 440 |  |  |  |  |

TABLE 2-continued

Soret band wavelengths

| Porphyrin | Soret band wavelength (nm) | | | | | | |
|---|---|---|---|---|---|---|---|
| | Control | HmuO | ChuS | HugZ | PigA | IsdI | IsdG |
| VO-meso-tetra-(N-methyl-4-pyridyl) | 422 | 422 | 422 | | | | |

Materials:

All oxygenase expression strains were BL21-DE3(T1) *E. coli* and pET28b plasmid based. Expression plasmids were constructed by inserting the gene for each oxygenase into the base vector pET28b. The gene for each enzyme was codon-optimized for expression in *E. coli* and synthesized by ThermoFisher®. Restriction sites HindIII and NotI were used on the 5' and 3' ends of each gene, to digest and insert them in-frame relative to a 5' HIS-tag. An Antarctic phosphatase pre-treatment, a 3:1 gene-insert:plasmid-backbone ratio, and QuickDNA® Ligase were used for all ligation reactions. Ligation products were subcloned into chemically competent Top10® *E. coli* and confirmed by sequencing through Genewiz® using SEQ ID NO: 13 & 14 primers. Plasmids from positive clones were transformed into the chemically competent BL21-DE3(T1) *E. coli* expression strain. Plasmid extractions were done using QIAprep® spin Miniprep kits and DNA purifications using QIAquick® PCR purification kits. All cloning and expression strains are stored at −80° C. in 25% glycerol stocks.

Liquid LB and LB-agar plates were used for culture growth. 100 μg/mL ampicillin (AMP100) or 50 μg/mL kanamycin (KAN50) was used for selection with strains harboring oxygenase gene-encoding ThermoFisher® plasmids or pET28b-based oxygenase expression vectors (respectively).

For expression of each plasmid, 5 mL of liquid LB-KAN50 was inoculated from a 25% glycerol −80° C. stock and grown overnight for 16 hrs. at 37° C. with shaking at 180 RPM. Non-baffled 250 mL flasks containing 50 mL of LB-KAN50 were inoculated with 100 μL from overnight cultures (1:500 dilution) and grown, at 37° C. and 180 RPM, to an optical density at 600 nm ($OD_{600}$) of 0.4-0.6 for induction. Oxygenase expression was then induced with 0.1 mM IPTG for 20 hrs. at room temperature and 90 RPM. Expression cultures were pelleted at 6 kRPM and 4° C. for 10 min. in an Avanti® J Series Centrifuge. Cell pellets were washed with phosphate-buffered saline (PBS), repelleted, supernatant decanted, and stored at −80° C. Cell pellets were resuspended in 5 mL protein storage buffer and lysed with 5×30 sec. pulses (30 sec. rests between each pulse) at 75% on ice. Cell debris was pelleted at 10 kRPM and 4° C. for 30 min. Protein-containing supernatants were transferred to chilled tubes in 1.5 mL aliquots. Protein lysates were stored at −80° C. for up to 3 months.

TABLE 3

Buffer compositions

| Solution | Ingredient | Concentration |
|---|---|---|
| Phosphate buffered saline | $NaHPO_4$ | 80 mM |
| | NaCl | 1.5M |
| | $KH_2PO_4$ | 20 mM |
| | KCl | 30 mM |

TABLE 3-continued

Buffer compositions

| Solution | Ingredient | Concentration |
|---|---|---|
| Protein storage buffer (pH 7.5) | Tris | 25 mM |
| | EDTA | 1 mM |
| | DTT | 5 mM |
| | Glycerol | 20% |
| Protein assay buffer | Tris | 25 mM |
| | EDTA | 100 μM |
| | DTT | 500 μM |
| Porphyrin phosphate buffer (pH 7.0) | $NaPO_4$-monobasic | 5 mM |
| | $NaPO_4$-dibasic | 5 mM |
| | NaCl | 185 mW |
| | $Na_2EDTA$ | 1 mM |
| Tris buffer (pH 7.8) | Tris | 20 mM |
| | NaCl | 500 mW |

To prepare crude protein, aliquots were thawed on ice and diluted 4-fold with protein assay buffer (PAB). To isolate purified oxygenases, protein aliquots were thawed on ice and proteins of interest were purified by HIS-tag-Ni-NTA column affinity followed by size exclusion chromatography with PD-10 desalting columns. Purified protein was eluted in PAB, collected in the first 2 mL PD-10 column flow-through fraction. Relative to the initial protein concentration, samples were diluted 4-fold to parallel crude protein samples.

Crude and purified protein quality was confirmed by gel separation and staining. Proteins were separated by size on a Bolt 4-12% Bis-Tris Plus gel in MES SDS running buffer, for 30 min. at 165 V and room temperature, stained with GelCode Blue Safe® Protein Stain for 1 hr. at 50 RPM and destained with water overnight at 50 RPM.

Model porphyrin stocks were prepared in porphyrin phosphate buffer (PPB), stored at 4° C. in amber bottles to protect samples from light, and used or discarded within one month.

Assay Conditions:

Amber tubes were used for all assays to protect samples from light. Crude and purified protein samples were combined with porphyrin substrates, to achieve final concentrations in Table 4, and total assay volumes were raised to 10 mL with Tris buffer. Absorbance of a 2.4 mL sample was measured in a 1 cm quartz cuvette, at room temperature, 1 nm resolution, and 0.7 sec. integration time on an Evolution201® UV-VIS spectrophotometer with Thermo INSIGHT® software. Samples were incubated for 24 hrs. at room temperature and 75 RPM and their final UV-VIS absorbance spectra was measured. An absorbance baseline was collected using Tris buffer at the beginning of each time point and ≤1% error was observed between technical replicates. Crude, empty pET28b vector (EV) strain lysate protein and PAB only controls were run in parallel with experimental samples (EXP) for each porphyrin.

TABLE 4

Porphyrin properties and details

| Porphyrin | Stock Conc. (mM) | Assay Conc. (μM) | Ascorbate conc (μM) |
|---|---|---|---|
| Hemin | 8 | 35 | 250 |
| Ni(II)-protoporphyrin (IX) | 100 | 50 | 1000 |
| Fe(III)-meso-tetra(4-carboxyphenyl) porphine | 50 | 10 | 100 |
| Ni(II)-meso-tetra(4-carboxyphenyl) porphine | 50 | 10 | 1000 |
| Ni(II)-meso-tetra(N-methyl-4-pyridyl) porphine tetrachloride | 50 | 10 | 1000 |
| VO-meso-tetra(N-methyl-4-pyridyl) porphine tetrachloride | 50 | 10 | 1000 |

Porphyrin Demetallation Calculation was calculated according to the formula $(EV_f - EXP_f) \pm EV_0 = \%$ enzyme specific demetallation.

Canonical Oxygenases:

Oxygenases have been identified in practically all organisms studied to date. A "canonical" mechanism of action has been defined using the human heme oxygenase as a reference. Enzymes using this mechanism have been identified in animal, plant, and bacterial cells and characterized such that the molecular details of their mechanisms are broadly accepted. Three bacterial enzymes whose canonical mechanisms have been biochemically and genetically characterized, and whose crystal structure has been solved are used in this study.

The effects of HmuO from *C. jeikeium* on the model porphyrins are shown in FIG. 1. High levels of active, full-length HmuO have been heterologously expressed in *E. coli* and the crystal structure has been solved. HmuO's substrate-free active site has been found to be slightly wider than that of other oxygenases. This may facilitate binding and demetallation of porphyrins with larger R-groups.

The effects of PigA from *P. aeruginosa* are shown in FIG. 2. Active, full length PigA has also been expressed in *E. coli* and the crystal structure has been solved. While PigA has a number of unique active site residues on the proximal and distal α-helices. These residues facilitate a novel substrate binding orientation, oxidation at the γ-meso carbon position and γ/β-regioselectivity. This substrate binding site has the potential to accommodate bulky R-groups of asymmetrical porphyrins.

The effects of HugZ from *H. pylori* are shown in FIG. 3. Active, full length and mutant HugZ has been expressed in *E. coli* and the crystal structure has been reported. A flexible loop of the C-terminus is responsible for binding and demetallating heme in HugZ's active site. This affords increased flexibility in the binding site and may facilitate binding of non-heme substrates and promote release of reaction products. This unique flexibility also makes the δ-meso carbon atom of hemin accessible in the HugZ active site, which leads to this enzyme's δ-meso regiospecificity. Furthermore, results from mutagenesis studies suggest that HugZ's active site histidine functions for specific recognition of and binding to Fe-containing heme, rather than contributing to the enzymatic demetallation mechanism as it does in canonical enzymes. This information suggests that the HugZ binding pocket may be able to accommodate a broad range of large petroporphyrin molecules.

Non-Canonical Oxygenases:

The effects of ChuS from *E. coli* are shown in FIG. 4. Although the mechanism of action of ChuS has yet to be detailed, its crystal structure has been solved. A histidine residue in ChuS's active site is located on a C-terminal α-helix distal to the active site and appears to be functionally essential. The active site is composed of a central set of antiparallel β-sheets, rather than a pair of α-helices. The enzymatic activity, although not yet characterized, has been observed in independently expressed N- and C-terminal halves of the enzyme.

The effects of IsdI from *S. aureus* are shown in FIG. 5, and those of IsdG are shown in FIG. 6. The crystal structures of IsdI and IsdG have been solved. The two enzymes have been overexpressed in *E. coli*. IsdI and IsdG from *S. aureus* possess active sites that are structurally and functionally similar to each other but unique relative to oxygenases. Although IsdG and IsdI both lack the glycine rich sequence and histidine residue that are characteristic of canonical active sites, their heme-degradation products are chromatographically similar to those generated by canonical reaction mechanisms, biliverdin and free iron. Rather than depending upon Fe(III)-OOH interactions with the active site's hydrogen-bonding network as canonical enzymes do, IsdI and IsdG achieve excessive steric interactions between heme and specific residues in the active site. The porphyrin undergoes significant distortion, or ruffling, from its natural planar geometry which induces ring opening, cleavage at the porphyrin ring's β- or γ-meso carbon, and demetallization.

TABLE 4

Sequence Correspondence Table

| SEQ ID NO | Protein | Organism |
|---|---|---|
| 1 | HmuO | *Corynebacterium jeikeium* |
| 2 | PigA | *Pseudomonas aeruginosa* |
| 3 | ChuS | *Escherichia coli* |
| 4 | ChuS | *Pseudomonas aeruginosa* |
| 5 | HugZ | *Helicobacter pylori* |
| 6 | IsdI | *Staphylococcus aureus* |
| 7 | IsdI | *Mycobacterium tuberculosis* |
| 8 | IsdI | *Bacillus thuringiensis* |
| 9 | IsdG | *Staphylococcus aureus* |
| 10 | IsdG | *Listeria monocytogenes* |
| 11 | IsdG | *Mycobacterium abscessus* |
| 12 | IsdG | *Bacillus cereus* |
|  | Construct |  |
| 13 |  | Forward cloning primer |
| 14 |  | Reverse cloning primer |

The invention claimed is:

1. A method comprising:
   i) providing a first hydrocarbon stream comprising aromatic molecules;
   ii) contacting the hydrocarbon stream with an oxygenase having a sequence identity to an oxygenase selected from the group consisting of SEQ ID Nos: 1-12; and
   iii) producing a second hydrocarbon stream having a reduced content of aromatic molecules from the first hydrocarbon stream.

2. The method of claim 1, wherein the oxygenase is substantially cell-free.

3. The method of claim 1, wherein the oxygenase is a recombinant enzyme.

4. The method of claim 1, wherein the oxygenase is capable of cleaving heteroatom-carbon bonds and carbon-carbon bonds in non-porphyrin compounds.

5. The method of claim 1, wherein the second hydrocarbon stream has a reduced content of at least one of nitrogen or sulfur.

6. The method of claim 1, wherein the hydrocarbon stream is crude oil or vacuum resid.

7. The method of claim 1, wherein the contacting is performed at a temperature from about 15° C. to about 90° C.

8. The method of claim 1, wherein the oxygenase is thermally stable from about 90° C. to about 120° C.

9. The method of claim 1, wherein there is less than 10 wt % loss of hydrocarbon following reduction of the aromatic molecules.

10. The method of claim 1, wherein the oxygenase is present in an oil reservoir, a pipeline, a tank, a vessel, and/or a reactor.

11. The method of claim 1, wherein the oxygenase is in free form, crystal form, or immobilized on a carrier.

12. The method of claim 11, wherein the carrier is selected from the group consisting of a membrane, a filter, a matrix, diatomaceous material, particles, beads, an ionic liquid, and a mesh.

13. The method of claim 12, wherein the matrix comprises a polymeric resin and/or a water wet protein.

14. The method of claim 12, wherein the particles and/or beads comprise a material selected from the group consisting of glass, ceramic, and a polymer.

15. The method of claim 1, wherein the oxygenase is hydrophobically modified to be at least 10% more enriched in hydrophobic amino acids selected from the group consisting of Ala, Gly, Ile, Leu, Met, Pro, Phe, and Trp.

16. The method of claim 15, wherein the enrichment is at least 20%.

17. The method of claim 15, wherein enrichment is achieved by replacing a native residue with the hydrophobic amino acid.

18. The method of claim 15, wherein enrichment is achieved by adding the hydrophobic amino acid between two native residues.

19. The method of claim 1, wherein the oxygenase is rinsed with n-propanol.

20. The method of claim 1, wherein the oxygenase is conjugated to a polyethylene glycol.

21. The method of claim 1, wherein disulfide bridges are added to the oxygenase.

22. The method of claim 1, wherein one to ten hydrophobic amino acid residues are added to an amino or carboxy terminus of the oxygenase, wherein the hydrophobic amino acid is selected from the group consisting of Ala, Gly, Ile, Leu, Met, Pro, Phe, and Trp.

23. The method of claim 1, wherein the first hydrocarbon stream comprises porphyrin molecules, and the contacting results in cleavage of at least a portion of the porphyrin rings at the β- or γ-mesa carbon.

24. The method of claim 1, wherein the first hydrocarbon stream comprises non-porphyrin molecules, and the contacting results in cleavage of heteroatom-carbon bonds or carbon-carbon bonds in at least a portion of the non-porphyrin molecules.

\* \* \* \* \*